United States Patent [19]
McEwen et al.

[11] Patent Number: 5,855,589
[45] Date of Patent: *Jan. 5, 1999

[54] PHYSIOLOGIC TOURNIQUET FOR INTRAVENOUS REGIONAL ANESTHESIA

[76] Inventors: James A. McEwen, 10551 Bamberton Drive, Richmond, B.C., Canada, V7A 1K6; Michael Jameson, 2365 Badger Road, North Vancouver, British Columbia, Canada, V7G 1S9

[ * ] Notice: The term of this patent shall not extend beyond the expiration date of Pat. No. 5,556,415.

[21] Appl. No.: 793,413

[22] PCT Filed: Aug. 25, 1995

[86] PCT No.: PCT/IB95/00777

§ 371 Date: Jun. 11, 1997

§ 102(e) Date: Jun. 11, 1997

[87] PCT Pub. No.: WO96/06568

PCT Pub. Date: Mar. 7, 1996

[51] Int. Cl.[6] .................................................. A61B 17/12
[52] U.S. Cl. ............................................. 606/202; 600/499
[58] Field of Search .................................. 606/201–202; 600/485–499

[56] References Cited

U.S. PATENT DOCUMENTS

| | | |
|---|---|---|
| 3,164,152 | 1/1965 | Vere Nicoll . |
| 3,319,623 | 5/1967 | London . |
| 3,825,008 | 7/1974 | Shook . |
| 4,106,002 | 8/1978 | Hogue, Jr. . |
| 4,168,063 | 9/1979 | Rowland . |
| 4,256,094 | 3/1981 | Kapp et al. . |
| 4,294,261 | 10/1981 | Baker et al. . |
| 4,321,929 | 3/1982 | Lemelson . |
| 4,326,536 | 4/1982 | Kitagawa et al. . |
| 4,469,099 | 9/1984 | McEwen . |
| 4,479,494 | 10/1984 | McEwen . |
| 4,520,819 | 6/1985 | Birmingham et al. . |
| 4,520,820 | 6/1985 | Kitchin et al. . |
| 4,533,346 | 8/1985 | Cosgrove, Jr. et al. . |
| 4,548,198 | 10/1985 | Mannes . |
| 4,605,010 | 8/1986 | McEwen . |
| 4,627,440 | 12/1986 | Ramsey, III et al. . |
| 4,635,635 | 1/1987 | Robinette-Lehman . |
| 4,667,672 | 5/1987 | Romanowski . |
| 4,671,290 | 6/1987 | Miller et al. . |
| 4,718,891 | 1/1988 | Lipps . |
| 4,770,175 | 9/1988 | McEwen . |
| 4,781,189 | 11/1988 | Vijil-Rosales . |
| 4,869,265 | 9/1989 | McEwen . |
| 4,883,462 | 11/1989 | Williamson . |
| 4,920,971 | 5/1990 | Blessinger . |
| 5,048,536 | 9/1991 | McEwen . |
| 5,103,833 | 4/1992 | Apple . |
| 5,108,363 | 4/1992 | Tuttle et al. . |
| 5,181,522 | 1/1993 | McEwen . |
| 5,254,087 | 10/1993 | McEwen . |
| 5,312,431 | 5/1994 | McEwen . |
| 5,556,415 | 9/1996 | McEwen et al. ........................ 600/499 |

FOREIGN PATENT DOCUMENTS

| | | |
|---|---|---|
| 2253789 | 9/1992 | United Kingdom . |
| 8300995 | 3/1983 | WIPO .................................... 606/202 |
| WO83/00995 | 3/1983 | WIPO . |

OTHER PUBLICATIONS

C.M. Holmes, "Intravenous Regional Neural Blockade," in Neural Blcokade, M.J. Counsins & P.O. Bridenbaugh, Eds., pp. 443, 459, J.b. Lippincott & Co., 1988.

ECRI, "Pneumatic Tourniquets Used for Intravenous Regional Anesthesia," Health Devices, Dec. 1982, pp. 48–49.

(List continued on next page.)

*Primary Examiner*—William Lewis
*Attorney, Agent, or Firm*—Hancock, Meinger & Porter LLP

[57] ABSTRACT

A physiologic tourniquet includes a safety interlock system for detecting any potentially hazardous attempt to change tourniquet cuff pressure during a procedure involving the use of two cuffs for intravenous regional anesthesia. The attempt to change pressure is prevented until the operator provides a timely and separate confirmation action.

24 Claims, 12 Drawing Sheets

OTHER PUBLICATIONS

S.C. Grice et al., "Intravenous Regional Anesthesia: Prevention of Leakage . . . ", Anesthseiology, vol. 65, pp. 316–320, 1986.

J.A.H.Davies et al., "Intravenous Regional Analgesia: Danger of the Congested Arm and the Value of Occlusion Pressure," Anaesthesia, 1983, vol. 39, pp. 416–421.

E.M. Brown et al., "Intravenous Regional Anesthia (Bier block): Review of 20 Years' Experience," Can. J. Anaesthesia, 1989, vol. 36, pp. 307–310.

J. Haasio, "Intravenous Regional Anesthesia of the Arm: Effect of the Technique of Exsanguination . . . ," Anaesthesia, vol. 44, pp. 19–21, 1989.

C. Sorbie and P. Chacha, "Regional Anaesthesia by the Intravenous Route," Brit. Med. J., 1965, 1, 957–960.

K.M. El–Hassan et al., "Venous Pressure and Arm Volume Changes During Simulated Bier's Block," Anmesthesia, 1984, 39:229–235.

B.A. Finegan & M.D. Bukht, "Venous Pressures inteh Isolated Upper Limb . . . ," Can. Anaesthesia Soc. J., 1984, 31:364–367.

R. Sukhani et al., "Lidocaine Disposition . . . With Different Tourniquet Deflation Technics," Anesth. Analg. 1989, 68:633–637.

W.L. Lehman et al., "Intravenous Lidocaine for Anesthesia in the Lower Extremity," J.B.J.S. 66–A, 1984, pp. 1056–1060.

J.H. Davies & A.J. Walford, "Intravenous Reginal Anesthesia for Foot Surgery," Aeta. An. Scand., 1986, 30:145–147.

L.N. Nusbaum, "IVRA for Surgery on the Foot and Ankle," Anesthesiology, 64:91–92, 1986.

G.S. Duncan, "The Use of IVRA in Podiatric Surgery," Foot Surg., vol. 25, 1986, pp. 411–415.

J. Duggan et al., "Venous Pressures in IVRA," Reg. Anes., 9:70–72, 1984.

T.A. Noel, "Prevention of Leak of Local Anesthesia From Under a Pneumatic Tourniquet," Anesthes., 66:449–450, 1987.

H. Finlay, "A Modification of Bier's Intravenous Analgesia," Anesthesia, 1977, 32:357–358.

SHEET 1

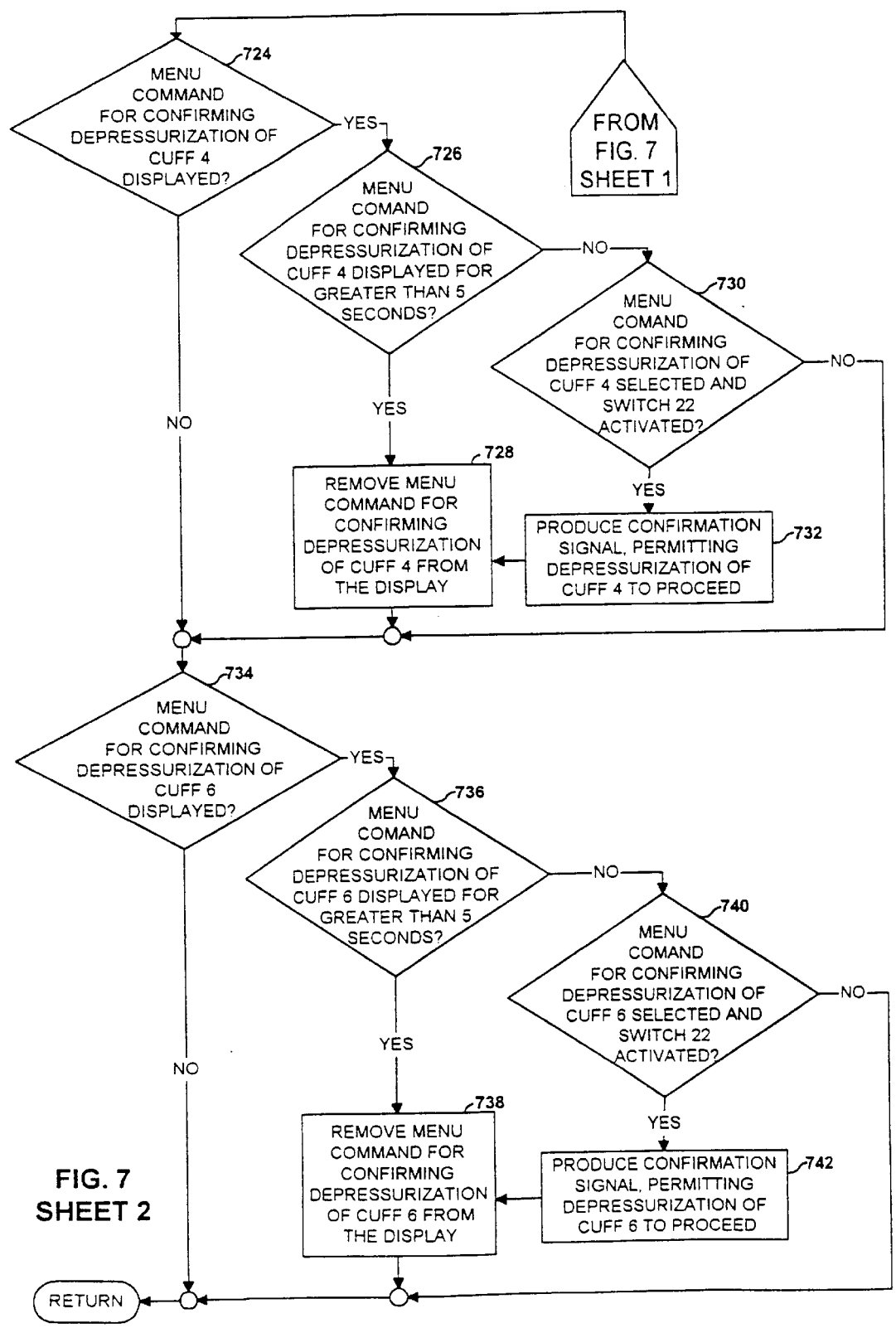

PHYSIOLOGIC TOURNIQUET FOR INTRAVENOUS REGIONAL ANESTHESIA

FIELD OF THE INVENTION

This invention pertains to automated tourniquet apparatus for use in surgery. In particular, the invention pertains to tourniquet apparatus having a safety interlock for improved safety in surgical procedures involving the use of intravenous regional anesthesia.

BACKGROUND OF THE INVENTION

This invention pertains to apparatus for improving safety in the administration and management of intravenous regional anesthesia (IVRA) for both upper and lower limbs. IVRA is an alternative to general anesthesia for limb surgery. IVRA has proven to be a simple and useful technique for satisfactorily anesthetizing the upper limb and is potentially well suited for greatly expanded utilization in surgery of lower limbs and in outpatient settings. In these settings, which are rapidly increasing in number worldwide, there is a large and unmet need for a rapid, simple, safe and reliable technique for establishing limb anesthesia. However, significant practical problems with the technology of IVRA in the prior art have limited the acceptance of this promising technique.

IVRA is an anesthetic technique which requires the use of a pneumatic surgical tourniquet system. Surgical tourniquet systems of the prior art typically include an inflatable cuff for encircling a limb and an automatic pressure regulator for maintaining a pressure applied by the cuff to the limb near a reference pressure selected by an operator or determined automatically. Surgical tourniquet systems are frequently used on the upper and lower limbs to help maintain a bloodless operative field by regulating the maximum pressure applied to the limb by an encircling cuff at a pressure sufficient to stop arterial blood flow past the cuff for the duration of a surgical procedure. A "physiologic tourniquet" system is generally considered to be one which has the capability of maintaining the pressure applied by the cuff to the limb near the minimum pressure required to stop the flow of arterial blood past the cuff during the surgical procedure.

During surgical procedures performed under IVRA, the surgical tourniquet system serves an additional role of preventing liquid anesthetic agent introduced into the veins in the limb distal to the cuff from flowing proximally past the cuff and out of the limb into the circulatory system. For surgical procedures where IVRA is to be employed, special cuffs having dual bladders are often used for encircling the limb, resulting in a first bladder encircling the limb above a second bladder which also encircles the same limb distal to the first bladder. Alternatively, two separate single-bladder cuffs can be applied to the same limb. To maintain the pressures applied by one dual-bladder cuff or two single-bladder cuffs near selected reference pressures, one tourniquet instrument having a dual-channel automatic pressure regulator may be employed, or two separate tourniquet instruments, each having one automatic pressure regulator, may be employed. Regardless of whether one dual-bladder cuff or two separate cuffs are used, and regardless of whether one dual-channel tourniquet instrument or two single-channel tourniquet instruments are used, surgical procedures involving IVRA are typically conducted as follows.

IVRA is typically administered as follows. A dual-bladder cuff is first applied to the limb on which surgery is to be performed, so that the first and second inflatable bladders of the cuff encircle the same limb, with the first cuff bladder being located proximal to the second, and so that both cuff bladders are located between the heart and the operative site on the limb. The portion of the limb distal to both bladders is then exsanguinated, often by wrapping the limb with an elastic bandage, beginning at the end of the limb and wrapping tightly towards the heart up to the cuff location. While the limb is thus exsanguinated, the tourniquet instrument is typically used to inflate the first (proximal) cuff and maintain it at a first predetermined cuff pressure sufficient to stop the inflow of arterial blood past the first cuff bladder. The elastic bandage is removed and a liquid anesthetic agent such as lidocaine mixed with sterile saline is introduced into a vein in the limb through an intravenous cannula. After a sufficient period of time has elapsed to allow tissue distal to the first cuff bladder to be anesthetised by the agent, the second pneumatic channel of the tourniquet instrument (or a second tourniquet instrument) is used to inflate the second (distal) cuff bladder and maintain it near a second predetermined pressure sufficient to stop the inflow of arterial blood past the second cuff bladder. The first (proximal) cuff bladder is then de-pressurized. In this manner, only the second cuff bladder remains inflated, it applies pressure primarily to anesthetised limb tissue encircled by the second bladder to reduce cuff-related pain, and the portion of the limb distal to the second cuff bladder remains anesthetised.

The anesthetic liquid is maintained in the veins in the limb distal to the second cuff bladder as long as the second cuff bladder remains pressurized to a sufficient pressure, thus maintaining the regional anesthesia in the limb distal to the second cuff bladder.

Occasionally during a surgical procedure involving the use of IVRA, an operator may intentionally change the pressures applied by one or both of the cuff bladders to the limb, and may intentionally de- pressurize one or both bladders of a dual-bladder cuff.

This is most common during long surgical procedures involving the use of IVRA. For example, because the probability of injury to nerves in the limb encircled by a pressurizing cuff bladder is known to increase with increased pressure applied by the cuff bladder to the limb, the operator may change the pressure applied by one or both of the cuff bladders to be a pressure near to the minimum pressure estimated to be required to stop the inflow of arterial blood past the cuff bladder.

Also, during a surgical procedure involving IVRA, the operator may re-pressurize the first (proximal) cuff bladder to a predetermined pressure and de-pressurize the second (distal) cuff bladder to a level near atmospheric pressure, in order to reduce cuff pain by moving the location of pressure applied to the limb and by allowing liquid anesthetic agent to re-infiltrate tissue beneath the location of the second (distal) cuff bladder. In long surgical procedures involving IVRA, this may be followed by re-pressurization of the first (proximal) cuff bladder to a predetermined level sufficient to stop blood flow and leakage of liquid anesthetic agent, and by de-pressurization of the second (distal) bladder to a pressure near atmospheric pressure. In certain other instances, the operator may intentionally pressurize both cuff bladders simultaneously to a predetermined reference pressure, for example, in order to distribute the applied pressure over a larger area in an effort to reduce cuff-related pain. In still other instances, the operator may intentionally reduce the pressure of both cuff bladders to a near-atmospheric level for a period of time, for example to allow blood to flow briefly before closing the surgical site in order to locate bleeding vessels which require suturing or to temporarily perfuse tissue distal to the cuff.

A potentially serious hazard of IVRA is that the operator may make an error in attempting to change the pressures applied by one or both of the cuff bladders to the limb, or may make an error in attempting to de-pressurize one or both bladders of the dual-bladder cuff. A serious error is one that causes both cuff bladders to be inadvertently deflated or depressurized simultaneously. Premature release of the liquid anesthetic agent soon after its introduction, as a result of the inadvertent deflation or depressurization of a cuff bladder so that both cuff bladders are at a pressure below the minimum pressure required to stop the inflow of arterial blood or the outflow of anesthetic liquid from the limb distal to both cuff bladders, is a serious and recognized hazard of prior art devices used for IVRA which may result in the anesthetic agent entering the circulatory system in a sufficiently high concentration to cause adverse reactions, including a range of minor adverse reactions and such serious adverse reactions as cardiovascular collapse, respiratory depression, epileptic-like seizures or even death.

Also, inadvertent deflation or depressurization of a cuff bladder so that both cuff bladders are at pressures below the minimum pressure required to stop the inflow of arterial blood or the outflow of anesthetic liquid from the limb distal to the cuff, at any time after introduction of the liquid anesthetic agent, is hazardous in that it will result in the reduction or elimination of the regional anesthesia in the limb distal to the cuff.

The applicant is unaware of any surgical tourniquet system in the prior art which includes apparatus for detecting a potentially hazardous attempt to change cuff pressure in a procedure involving the use of IVRA that may result in the release of liquid anesthetic agent from the limb into systemic circulation. Further, the applicant in unaware of any surgical tourniquet system in the prior art which, having detected such a potentially hazardous condition, will alert the operator to the hazardous condition and will require a separate and discrete confirmation action by the operator before changing the cuff reference pressure to the potentially hazardous level.

Finally, another hazard resulting from the use of prior-art tourniquet systems for IVRA is that internal malfunctions or failures of the apparatus may occur and compromise patient safety.

SUMMARY OF THE INVENTION

The present invention provides a physiologic tourniquet apparatus having a safety interlock for improved safety in surgical procedures involving the use of IVRA, wherein the safety interlock detects any potentially hazardous attempt to change cuff pressure in a procedure involving the use of IVRA that, if implemented by changing the cuff pressure, may result in the release of liquid anesthetic agent from the limb into systemic circulation.

The present invention also includes apparatus which will alert the operator to the potentially hazardous condition and which will require a separate and discrete confirmation action by the operator before changing the pressure applied by the cuff to the potentially hazardous level.

The present invention also includes apparatus for disabling the safety interlock so that the safety interlock may be disabled during surgical procedures such as bilateral limb procedures which may involve the use of a dual-channel tourniquet system, or two separate one-channel tourniquet systems, but which may not involve the use of IVRA.

The present invention includes a safety circuit for detecting and responding safely to certain malfunctions within the apparatus.

DESCRIPTION OF THE PREFERRED EMBODIMENT

The embodiment illustrated is not intended to be exhaustive or limit the invention to the precise form disclosed. It is chosen and described in order to explain the principles of the invention and its application and practical use, and thereby enable others skilled in the art to utilize the invention. The preferred embodiment of the invention is described in three sections below: hardware; operation and software.

I. Hardware

Figure 1:
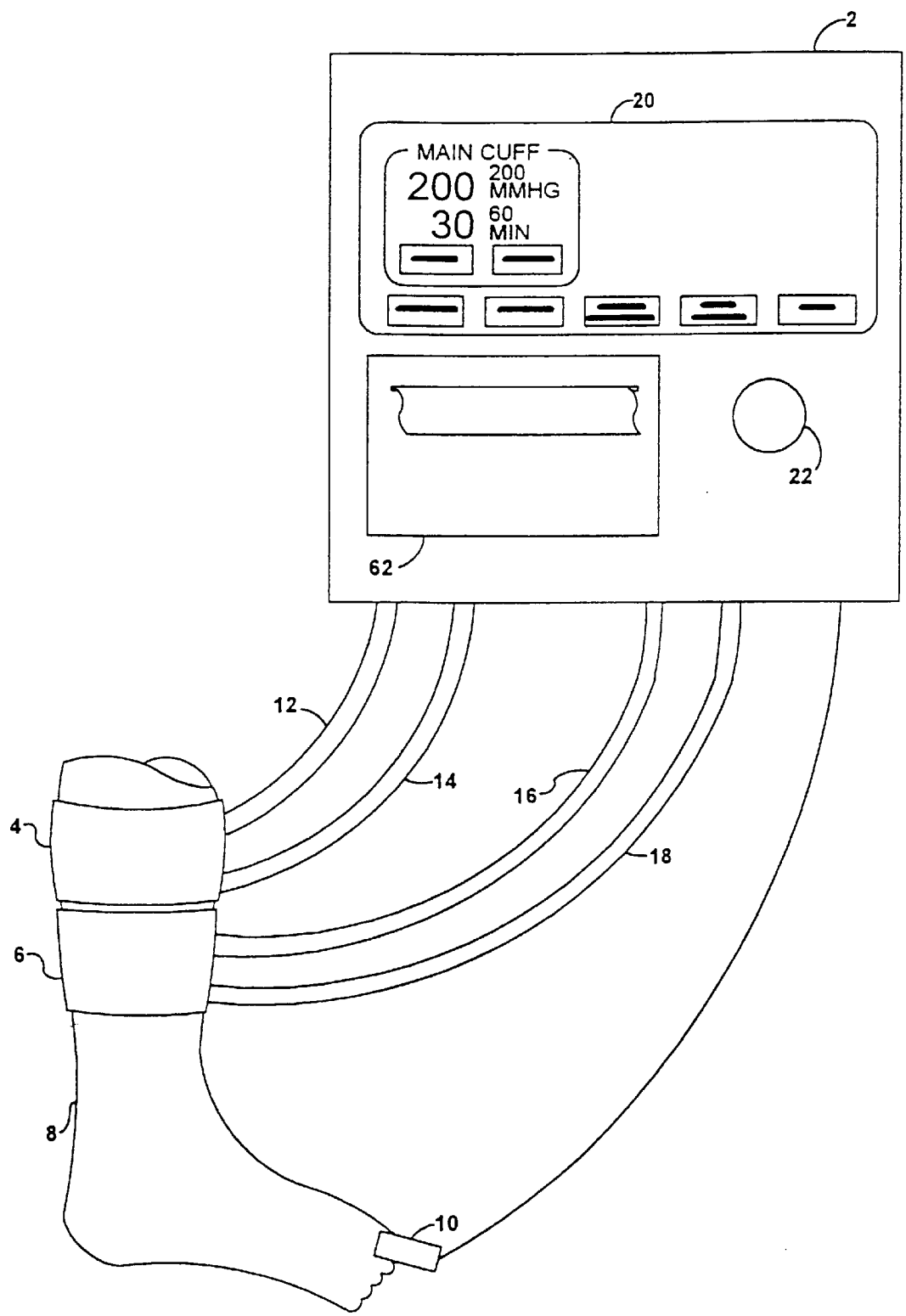
FIG. 1 is a pictorial representation of the preferred embodiment in a surgical application.

FIG. 1 depicts instrument 2 connected to pressurizing cuff 4 and pressurizing cuff 6, which cuffs can be inflated to apply pressures to patient limb 8. In FIG. 1, photoplethysmographic blood flow sensor 10 is shown applied to a digit of limb 8 distal to cuff 4 and cuff 6, and connected to instrument 2. For clarity, cuff 4 and cuff 6 have been shown as separate cuffs applied to the same limb 8, but in practice the separate cuffs may be applied to different limbs of a patient, or they may be combined as separate bladders of one dual-bladder inflatable cuff applied to a single limb of a patient, depending upon the surgical procedure being performed and the type of anesthesia employed. In many types of surgical procedures, only cuff 4 is employed and cuff 6 is not used.

As can be seen in FIG. 1, cuff 4 is connected pneumatically by tubing 12 and tubing 14 to instrument 2. Cuff 6 is connected pneumatically by tubing 16 and tubing 18 to instrument 2.

Figure 2:
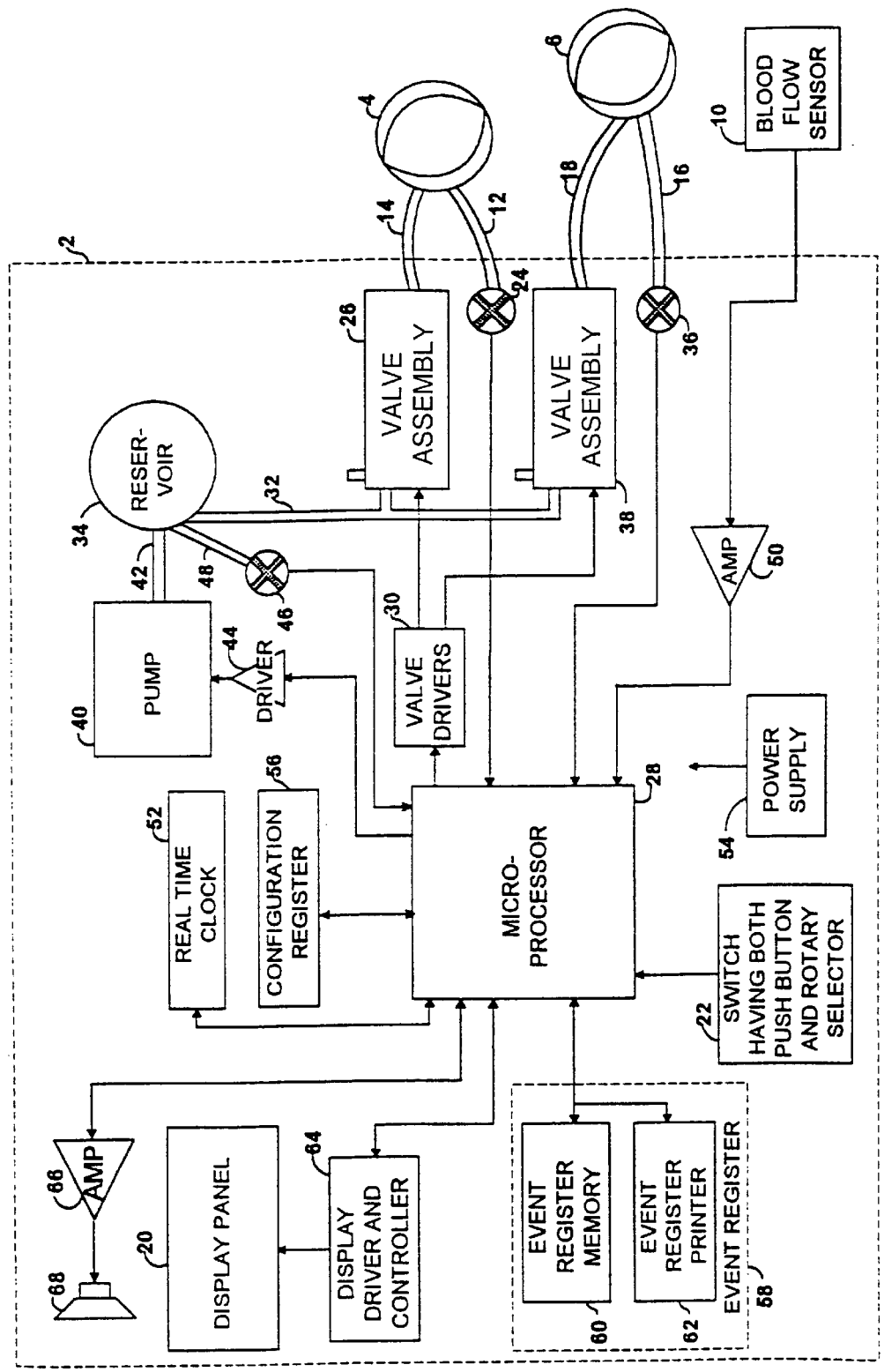
FIG. 2 is a block diagram of the preferred embodiment.

Electroluminescent graphic display panel 20 (EL4737LP, Planar Systems, Beaverton, Oreg.) shown in FIGS. 1 and 2 forms part of instrument 2 and is used to display information to the user of instrument 2. Display panel 20 is employed for the selective presentation of any of the following information as described below: (a) menus of commands for controlling instrument 2, from which a user may make selections; (b) parameters having values which characterize the actual cuff pressures, cuff inflation times, cuff pressure reference levels and inflation time alarm limit values; (c) text messages describing current alarm conditions, when alarm conditions are determined by instrument 2; (d) graphical representations of blood flow signals produced by sensor 10; and (e) messages which provide operating information to the user.

Switch 22 (61-01032-10 Grayhill Inc., La Grange, Ill.) shown in FIGS. 1 and 2, provides a versatile means for the user to control instrument 2. Switch 22 is a rotary selector and push-button combination switch. In combination with the electronic circuitry and software described below, switch 22 operates by producing signals in response to rotation of the selector and activation of the push-button by the user. In the preferred embodiment, rotating switch 22 allows the user to select a specific menu command or parameter for adjustment from those shown on display panel 20. The currently selected menu command or parameter is "highlighted" by being displayed in reverse video. If a menu command is "highlighted", pushing then releasing switch 22 causes the action indicated by the menu command to be performed. If a parameter is "highlighted", the value of the parameter can then be adjusted by pushing and releasing switch 22, and then rotating switch 22: clockwise rotation will cause the value of the parameter to be increased; counter-clockwise rotation will cause the value of the parameter to be decreased; pushing and releasing the switch 22 again completes the adjustment of the parameter, and allows other menu commands or parameters to be selected in response to subsequent rotation of switch 22.

As can be seen in FIG. 2, cuff 4 is connected pneumatically by tubing 12 to pressure transducer 24, and is connected pneumatically by tubing 14 to valve assembly 26. Valve assembly 26 is shown in detail in FIG. 10 and further described below.

Valve assembly 26 responds to certain signals generated by microprocessor 28 (80C196KB, INTEL Corp., Santa Clara, Calif.) to pneumatically connect tubing 14 through tubing 32 to gas pressure reservoir 34, a sealed pneumatic chamber having a fixed volume of 500 ml. Valve assembly 26 also responds to other signals generated by microprocessor 28 to pneumatically connect tubing 14 to atmosphere, allowing the release of pressure in cuff 4. Valve sensing circuit 1020 (FIG. 10) included in valve assembly 26 responds to a cuff 4 mode signal generated by microprocessor 28 which is indicative of a predefined cuff mode; in the preferred embodiment three cuff modes for cuff 4 are defined: "cuff inflating" mode, "cuff regulating" mode and "cuff deflating" mode. The level to which the cuff 4 mode signal is set by microprocessor 28 is determined by user input and microprocessor 28. Pressure transducer 24 generates a cuff 4 pressure signal which indicates the pressure of gas in cuff 4, and the cuff 4 pressure signal is then communicated to an analog to digital converter (ADC) input of microprocessor 28 which digitizes the cuff pressure signal. When the cuff 4 mode signal is at a level indicative of "cuff inflating" mode, microprocessor 28 acts to increase the level of pressure within cuff 4 from a level near atmospheric pressure to a level near the reference pressure represented by the cuff 4 reference pressure signal, by generating signals for the actuation of valves 1002 and 1004 (FIG. 10) within valve assembly 26, thereby pneumatically connecting cuff 4 to a gas pressure reservoir 34. When the cuff 4 mode signal is at a level indicative of "cuff regulating" mode microprocessor 28 acts to regulate the pressure within cuff 4 near the reference pressure represented by the cuff 4 reference pressure signal by generating signals for the selective actuation of either valves 1002 or valve 1006 (FIG. 10) within valve assembly 26, thereby pneumatically connecting cuff 4 to gas pressure reservoir 34 or pneumatically connecting cuff 4 to atmosphere. When the cuff 4 mode signal is at a level indicative of "cuff deflating" mode, microprocessor 28 acts to reduce the level of pressure within cuff 4 to a level near atmospheric pressure by generating signals for the actuation of valves 1006 and 1010 (FIG. 10) within valve assembly 26, thereby pneumatically connecting cuff 4 to atmosphere. To alert the user if the pressure in cuff 4 can not be regulated within a pre-assigned limit of ±15 mmHg, microprocessor 28 compares the cuff pressure signal from cuff pressure transducer 24 to the reference pressure signal for cuff 4. If the cuff pressure signal exceeds the reference signal by 15 mmHg or more, microprocessor 28 generates an alarm signal indicating over-pressurization of cuff 4. If the cuff pressure signal is less than the reference pressure signal by a difference of 15 mmHg or more, microprocessor 28 generates an alarm signal indicating under-pressurization of cuff 4. Microprocessor 28 also tracks the inflation time for cuff 4, by maintaining a counter indicating the length of time that cuff 4 has been pressurized. Microprocessor 28 compares this actual cuff inflation time to an inflation time limit for cuff 4, and if the actual cuff inflation time exceeds the inflation time limit, microprocessor 28 generates an alarm signal indicating that the inflation time limit for cuff 4 has been exceeded.

Figure 10:
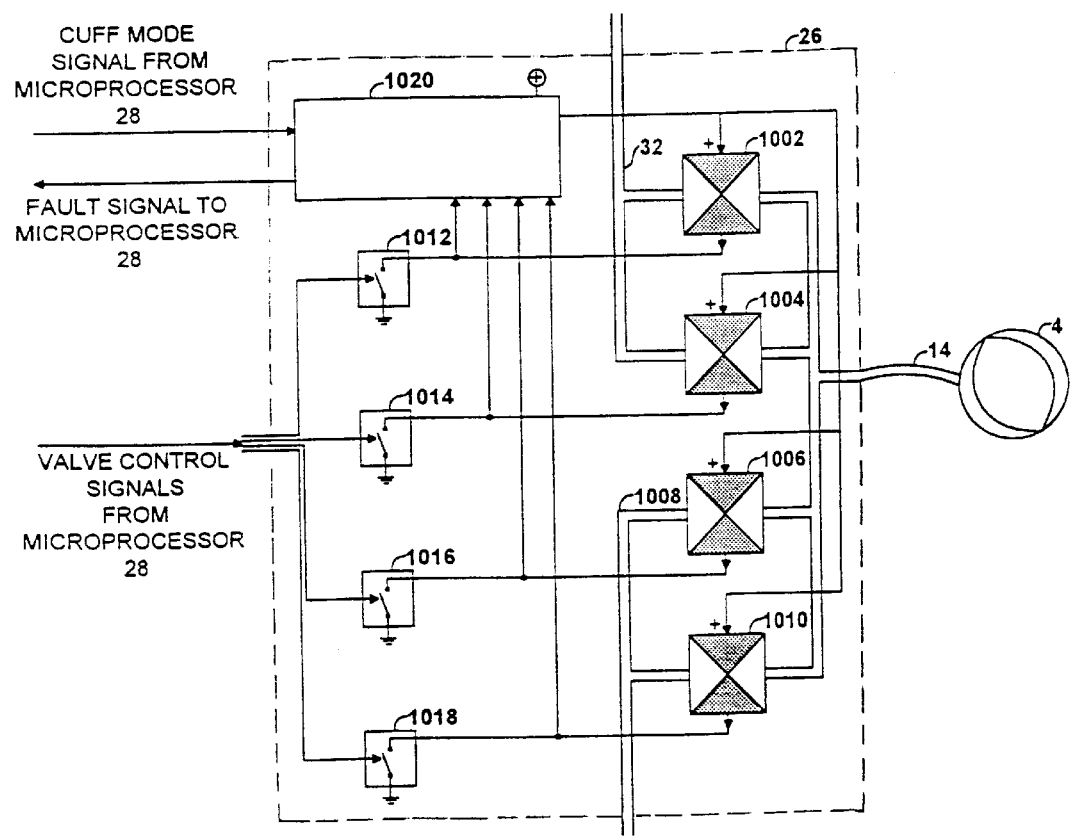
FIG. 10 is a block diagram of a valve assembly of the preferred embodiment.

As depicted in FIG. 2, if cuff 6 is required for the surgical application, cuff 6 is connected pneumatically by tubing 16 to pressure transducer 36, and is connected pneumatically by tubing 18 to valve assembly 38. Valve assembly 38 has the same structure as valve assembly 26 which is described in detail below and which is shown in FIG. 10. Valve assembly 38 responds to signals described below which are generated by microprocessor 28, to pneumatically connect tubing 18 through tubing 32 to gas pressure reservoir 34. Valve assembly 38 also responds to other signals described below which are generated by microprocessor 28 to pneumatically connect tubing 18 to atmosphere, allowing the release of pressure in cuff 6. Valve assembly 38 responds to a cuff 6 mode signal generated by microprocessor 28 which is indicative of a predefined cuff mode; in the preferred embodiment three modes for cuff 6 are predefined: "cuff inflating" mode, "cuff regulating" mode, and "cuff deflating" mode. The level is to which the cuff 6 mode signal is set by microprocessor 28 is determined by user input and microprocessor 28.

Pressure transducer 36 generates a cuff 6 pressure signal which indicates the pressure of gas in cuff 6, and the cuff 6 pressure signal is then communicated to an analog to digital converter (ADC) input of microprocessor 28 which digitizes the cuff 6 pressure signal. When the cuff 6 mode signal is at a level indicative of "cuff inflating" mode, microprocessor 28 acts to increase the level of pressure within cuff 6 from a level near atmospheric pressure to a level near the reference pressure represented by the cuff 6 reference pressure signal, by generating signals for the actuation of selected valves within valve assembly 38. When the cuff 6 mode signal is at a level indicative of "cuff regulating" mode microprocessor 28 acts to regulate the pressure within cuff 6 near the reference pressure represented by the cuff 6 reference pressure signal by generating signals for the actuation of selected valves within valve assembly 38. When the cuff 6 mode signal is at a level indicative of "cuff deflating" mode, microprocessor 28 acts to reduce the level of pressure within cuff 6 to a level near atmospheric pressure by generating signals for the actuation of certain valves within valve assembly 38. To alert the user if the pressure in cuff 6 can not be regulated within a pre-assigned limit of ±15 mmHg, microprocessor 28 compares the cuff pressure signal from cuff pressure transducer 36 to the reference pressure signal for cuff 6: if the cuff pressure signal exceeds the reference signal by 15 mmHg or more, microprocessor 28 generates an alarm signal indicating over-pressurization of cuff 6. If the cuff pressure signal is less than the reference pressure signal by a difference of 15 mmHg or more, microprocessor 28 generates an alarm signal indicating under-pressurization of cuff 6. Microprocessor 28 also tracks the inflation time for cuff 6, by maintaining a counter indicating the length of time that cuff 6 has been pressurized. Microprocessor 28 compares this actual cuff inflation time to an inflation time limit for cuff 6, and if the actual cuff inflation time exceeds the inflation time limit, microprocessor 28 generates an alarm signal indicating that the inflation time limit for cuff 6 has been exceeded.

As shown in FIG. 2, pneumatic pump 40 (E series 801105, Gilian Instrument Corp. Caldwell, N.J.) is pneumatically connected to reservoir 34 by tubing 42. Pump 40 acts to pressurize reservoir 34 in response to control signals from microprocessor 28 communicated through pump driver 44. Reservoir pressure transducer 46 is pneumatically connected through tubing 48 to reservoir 34 and generates a reservoir pressure signal indicative of the pressure in reservoir 34. The reservoir pressure signal is communicated to an ADC input of microprocessor 28. In response to this reservoir pressure signal and a reservoir pressure reference signal provided as described below, microprocessor 28 generates control signals for pump driver 44 and regulates the pressure in reservoir 34 to a pressure near the reference pressure represented by the reservoir reference pressure signal as described below.

Photoplethysmographic blood flow sensor 10 is placed on a portion of a limb distal to cuff 4, and distal to cuff 6 if cuff 6 is also employed, to sense blood flow beneath the flow sensor 10. FIG. 1 illustrates a typical location of sensor 10 for the lower limb. Sensor 10 generates a blood flow signal indicative of blood flow beneath the sensor, which is processed by amplifier 50 and communicated to an ADC input of microprocessor 28, as depicted in FIG. 2.

Real time clock 52 shown in FIG. 2 maintains the current time and date, and includes a battery as an alternate power source such that clock operation continues during any interruption in the supply of electrical power from power supply 54 required for the normal operation of instrument 2. Microprocessor 28 communicates with real time clock 52 for both reading and setting the current time and date.

Configuration register 56 shown in FIG. 2 is comprised of non-volatile memory (24LC02, Microchip Technology, Chandler Ariz.) operating in conjunction with microprocessor 28 as described below to contain previously recorded cuff reference pressure levels and inflation time alarm limits for use by microprocessor 28 as described below, and retains these recorded levels of these parameters indefinitely in the absence or interruption of electrical power from power supply 54 required for the normal operation of instrument 2. The levels of the cuff reference pressures and inflation time limits initially recorded in configuration register 56 are given in the table below:

alarm signal as described above; and (c) events associated with determining a cuff pressure automatically as described below. Event register 58 comprises event register memory 60 (28C64A Microchip Technology, Chandler, Ariz.), and event register printer 62. Microprocessor 28 communicates with event register 58 to record events as they occur. Microprocessor 28 records an event by communicating to event register 58: the time of the event as read from real time clock 52; a value identifying which one of a specified set of events occurred as determined by microprocessor 28; and the values at the time of the event of the following parameters: operating mode signal, cuff 4 pressure signal; cuff 4 pressure reference signal; cuff 4 inflation time, cuff 4 inflation time limit; cuff 6 pressure signal; cuff 6 pressure reference signal; cuff 6 inflation time, cuff 6 inflation time limit; and recommended cuff pressure, when the event occurred. Entries are recorded in event register 58 by storing values in event register memory 60 and by printing these values for the user by means of event register printer 62. Event register memory 60 retains information indefinitely in the absence or interruption of electrical power from power supply 54 required for the normal operation of instrument 2.

Microprocessor 28 communicates with electroluminescent display panel 20 through display controller 64 to display information as described above.

User input is by means of switch 22. Signals from switch 22 arising from rotation and push-button contact closure in switch 22 are communicated to microprocessor 28.

Microprocessor 28 will, in response to generated alarm signals alert the user by text and graphic messages shown on display panel 20 and by audio tones. Electrical signals having different frequencies to specify different alarm signals and conditions are produced by microprocessor 28, amplified by audio amplifier 66 and converted to audible sound by loud speaker 68 shown in FIG. 2.

Power supply 54 provides regulated DC power for the normal operation of all electronic and electrical components.

Shown in FIG. 10 and described below is a detailed block diagram of valve assembly 26 shown in FIG. 2. When actuated, valve 1002 (EVO-3-60V Clippard Instrument Laboratory, Cincinnati, Ohio) pneumatically connects tubing 32 to tubing 14, permitting the flow of gas from reservoir 34 shown in FIG. 2 to cuff 4. Valve 1004 (201A3/30F Burkert Contromatic Corp., Orange, Calif.) when actuated also pneumatically connects tubing 32 to 14. The valve

| Operating Mode | Cuff 4 reference pressure | Cuff 4 inflation time limit | Cuff 6 reference pressure | Cuff 6 inflation time limit |
| --- | --- | --- | --- | --- |
| Single Cuff Mode | 200 mmHg | 60 Min. | — | — |
| Dual Cuff Mode | 200 mmHg | 60 Min. | 200 mmHg | 60 Min. |
| IVRA Dual Bladder Cuff Mode | 250 mmHg | 45 Min | 250 mmHg | 45 Min. |

Microprocessor 28 communicates with configuration register 56 to record and retrieve levels of the configuration parameters recorded in configuration register 56 as described below.

Event register 58 shown in FIG. 2, records "events" which are defined in the software of the preferred embodiment to be: (a) actions by the user to inflate a cuff, deflate a cuff, adjust the level of a cuff reference pressure signal, adjust the level of cuff inflation time limit signal, adjust the level of the operating mode signal or silence an audio alarm; (b) alarm events, resulting from microprocessor 28 generating an orifice of valve 1004 is substantially larger than the valve orifice of valve 1002 and therefore permits gas to flow into cuff 4 at a greater rate than valve 1002.

Valve 1006 (EVO-3-60V Clippard Instrument Laboratory, Cincinnati, Ohio) when actuated pneumatically connects tubing 14 to tubing 1008. Tubing 1008 is open to atmosphere and permits gas to be released from cuff 4. Valve 1010 (201A3/30F Burkert Contromatic Corp., Orange, Calif.) when actuated also pneumatically connects tubing 14 to tubing 1008. The valve orifice of valve 1010 is substantially larger than the valve orifice of valve 1006 and therefore permits gas to be released from cuff 4 at a greater rate than valve 1006. This combination of valves permits cuff 4 to be inflated and deflated rapidly through valves 1004, 1010, and also permits the pressure in cuff 4 to be regulated accurately when inflated through valves 1002, 1006. Valve drivers 1012, 1014, 1016 and 1018, under the control of signals from microprocessor 28, complete an electrical circuit allowing electrical power to be applied for the actuation of valves 1002, 1004, 1006 and 1010 respectively.

Valve sensing circuit 1020 in valve assembly 26 monitors the actuation of valves 1002, 1004, 1006 and 1010 by monitoring the voltage levels between the valve drivers and the valves. If any one of the predetermined set of undesired valve actuations described below is detected, valve sensing circuit 1020 responds by generating a "fault" signal that is sent to microprocessor 28. Valve circuit 1020 also responds by disconnecting the supply of electrical power to all valves 1002, 1004, 1006, and 1010, thus de-actuating valves 1002, 1004, 1006 and 1010. De-actuating valves 1002, 1004, 1006 and 1010, ensures that the pressure within cuff 4 will remain will remain stable and not increase or decrease to unsafe levels as the result of an abnormal or undesired valve actuation. Microprocessor 28 responds to the "fault" signal by generating an alarm signal indicating that a valve related fault has occurred. Undesired valve actuations may result from the failure of any one of valve drivers 1012, 1014, 1016 or 1018, or failure of any one of valves 1002, 1004, 1006 and 1010, or a failure in microprocessor 28, or a software error. The table below summarizes the undesired combinations of valve actuations which are detected by valve sensing circuit 1020 for the three valid levels of the cuff mode signal.

| CUFF MODE SIGNAL | Valve 1002 | Valve 1004 | Valve 1006 | Valve 1010 |
| --- | --- | --- | --- | --- |
| Cuff Deflating Mode | actuated | x | x | x |
| Cuff Deflating Mode | x | actuated | x | x |
| Cuff Deflating Mode | x | x | de-actuated | de-actuated |
| Cuff Inflating Mode | x | x | actuated | x |
| Cuff Inflating Mode | x | x | x | actuated |
| Cuff Inflating Mode | de-actuated | de-actuated | x | x |
| Cuff Regulating Mode | actuated | x | actuated | x |
| Cuff Regulating Mode | x | actuated | x | x |
| Cuff Regulating Mode | x | x | x | actuated | x = either actuated or de-actuated

In the preferred embodiment, valve sensing circuit 1020 depicted in FIG. 10 also responds to a cuff mode signal generated by microprocessor 28. In the preferred embodiment, the level of the cuff mode signal for cuff 4 corresponds to one of three predefined levels, each of which is indicative of one of three modes: "cuff inflating" mode, "cuff regulating" mode and "cuff deflating mode". The cuff regulating mode refers to a mode of operation in which the cuff is maintained at a preselected pressure by the system. The level of the cuff mode signal determines which combinations of valve actuations will be classified as undesired by the valve sensing circuit 1020. Upon detecting an undesired valve combination, or upon detecting a cuff mode signal having a level other than one of three predefined levels indicative of the three valid cuff modes, valve sensing circuit 1020 generates a "fault" signal and disconnects the electrical power supplied to valves 1002, 1004, 1006 and 1010, thereby de-actuating valves 1002, 1004, 1006 and 1010. Deactuation of these valves maintains the prior status of the system, and reduces the likelihood of occurrences of such undesired events as simultaneous inflation and deflation of a cuff. An invalid cuff mode signal may result from the failure of microprocessor 28 or a software error.

II. Operation

At start-up of instrument 2, when instrument 2 is activated by supply of electrical power through power supply 54 microprocessor 28 configures instrument 2 by setting predetermined parameters to the levels recorded in configuration register 56. Configuration register 56 contains a previously recorded level for the operating mode signal and, for each of the three possible levels of the operating mode signal, previously recorded level for the cuff reference pressure and cuff inflation time alarm limit for each cuff, as described elsewhere. The user of instrument 2 can alter a level of a parameter recorded in configuration register 56, by selecting the parameter and changing its level as described below.

In operation, a user of the preferred embodiment communicates with instrument 2 by using switch 22 to choose commands for controlling instrument 2 from menus of commands, and by using switch 22 to set the level of parameters displayed on display panel 20, as described above and in the software description below.

Three distinct modes of operation of the preferred embodiment are provided in the preferred embodiment: "Single Cuff Mode", "Dual Cuff Mode" and "IVRA Dual-Bladder Cuff Mode". Microprocessor 28 controls the operation of instrument 2 in response to the level of the operating mode signal as described below. The level of the operating mode signal is set by microprocessor 28 retrieving a previously recorded level from configuration register 56 and can be altered by the user by means of switch 22 as described below.

Figure 3A:
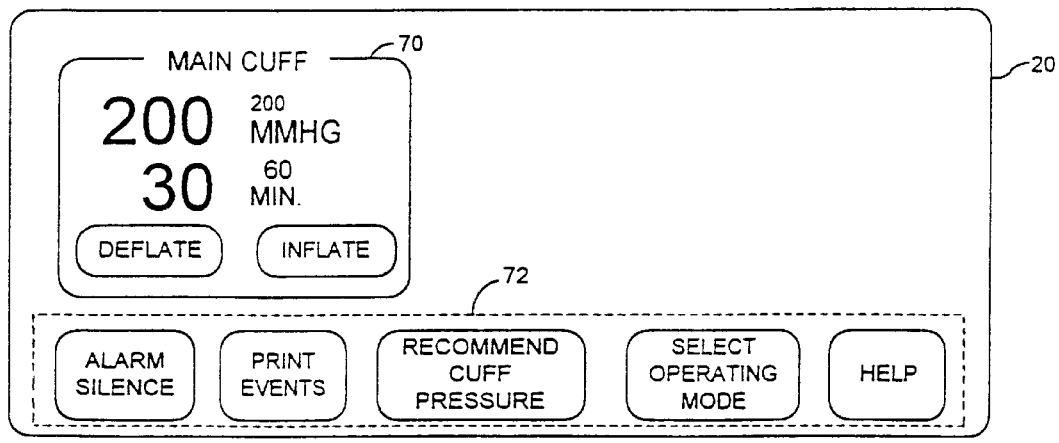
FIGS. 3a, 3b, 3c and 3d are pictorial representations of the layout of the display panel of the preferred embodiment in different clinical applications

FIG. 3a shows the layout of display panel 20 for "Single Cuff Mode", wherein only cuff 4 is actuated and used in a surgical procedure. As depicted in FIG. 3a, a single display region 70 labeled MAIN CUFF is shown on display panel 20 and predetermined menu 72 is also displayed for the user. Menu 72 enables choices to be made by the user for: temporarily silencing audio alarms; printing on event register printer 62 the events recorded in event register memory 60; initiating the determination of recommended cuff pressure; selecting an operating mode, or obtaining operating instructions. Menu 72 is depicted in FIG. 3a with the menu command "SELECT OPERATING MODE" shown in reverse video, indicating that it has been selected by the user of instrument 2. As shown in FIG. 3a, within display region 70 labeled MAIN CUFF parameters and menu commands for controlling cuff 4 are displayed, and all displayed parameters are continually updated by microprocessor 28. The displayed parameters are: the current level of cuff pressure, cuff pressure reference level, cuff inflation time and inflation time alarm limit level. The menu commands for control of cuff 4 are: "inflate" and "deflate". If the user selects the command "inflate", instrument 2 will regulate the pressure in cuff 4 near the level of the cuff 4 reference pressure signal as described above. If the user selects the command "deflate" instrument 2 will release the pressure in cuff 4 causing cuff 4 to deflate to atmospheric pressure. In "Single Cuff Mode" all alarm and event messages refer only to cuff 4.

Figure 3B:
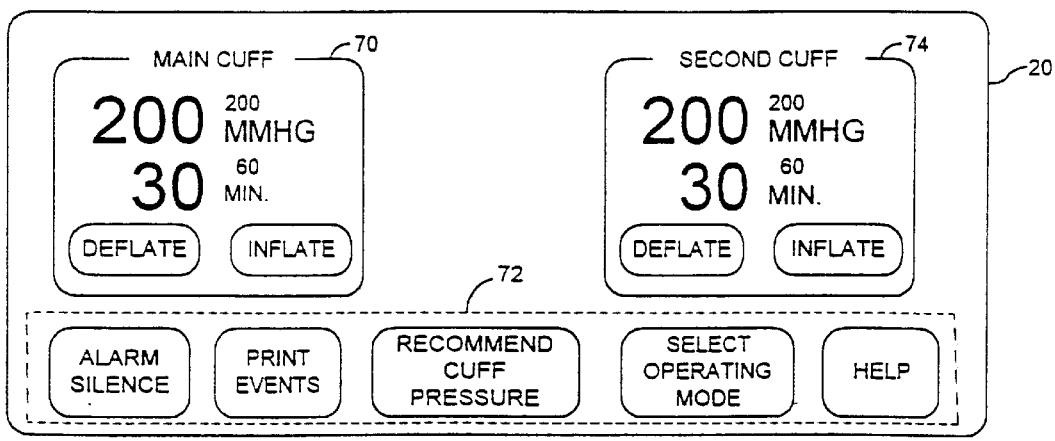

FIG. 3b depicts the layout of display panel 20 for "Dual Cuff Mode", corresponding to the second of three predetermined levels of the operating mode signal. In "Dual Cuff Mode" both cuff 4 and cuff 6 are actuated. As illustrated in FIG. 3b two independent display regions are shown on display panel 20, as well as the predetermined user menu 72 described above. One region 70 is labeled MAIN CUFF, within which region are displayed the parameters and menu commands for control of cuff 4. The second region 74 is labeled SECOND CUFF, within which region are displayed the parameters and controls for cuff 6. The parameters and controls displayed in region 74 are identical to those described above for cuff 4, except the parameters and controls displayed in region 74 refer to cuff 6. In "Dual Cuff Mode", the inflation and deflation of cuff 4 is independent of the inflation and deflation of cuff 6. All alarm and event messages refer either to cuff 4, the MAIN CUFF or to cuff 6, the SECOND CUFF. When cuff 6 is inflated in the "Dual Cuff Mode", the operating mode signal cannot be changed by the user until such time as cuff 6 has been deflated.

Figure 3C:
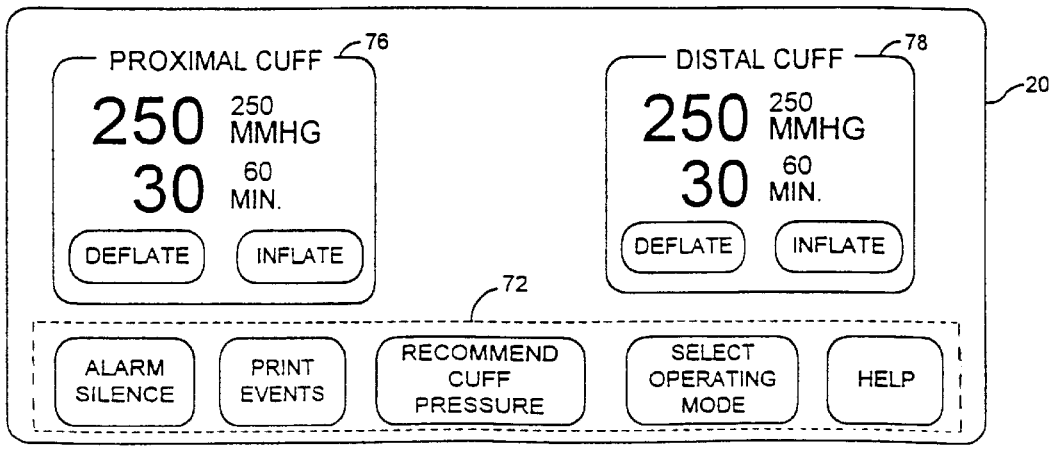

FIG. 3c depicts the layout of display panel 20 for the "IVRA Dual-Bladder Cuff Mode", corresponding to the third level of the operating mode signal. This mode can only be selected by the user when both cuff 4 and cuff 6 are deflated. The "IVRA Dual-Bladder Cuff Mode" is the preferred mode for selection by the user when Intravenous Regional Anesthesia (IVRA) also known as Bier block anesthesia, is employed. In "IVRA Dual-Bladder Cuff Mode" both cuff 4 and cuff 6 are actuated. As shown in FIG. 3c two independent display regions 76 and 78 are shown on display panel 20, also shown is predetermined user menu 72 having the structure and function as described above. Region 76, labeled PROXIMAL CUFF contains displays of parameters and controls for cuff 4. Region 78, labeled DISTAL CUFF contains displays of the parameters and controls for cuff 6. Alarm and event messages are generated to refer separately either to cuff 4, the PROXIMAL CUFF, or to cuff 6 the DISTAL CUFF. When the preferred embodiment is operating in "IVRA Dual-Bladder Mode", the operating mode signal cannot be changed by the user while either cuff 4 or cuff 6 is inflated.

In "IVRA Dual-Bladder Cuff Mode" a safety interlock is activated to reduce the probability of unintended and inadvertent deflation of both cuffs during a surgical procedure involving IVRA. The safety interlock operates as follows: if the user initiates deflation of cuff 4 while cuff 6 is deflated, or if the user initiates deflation of the cuff 6 while cuff 4 is deflated, a safety interlock signal is produced to prevent the initiated deflation and a visual and audible warning is given via display panel 20 and speaker 68 to indicate to the user that the action the user has initiated may be unsafe, i.e. that the action would result in cuff 4 and cuff 6 being deflated at a time in a surgical procedure involving IVRA when liquid anesthetic agent contained in blood vessels distal to cuff 4 and cuff 6 may be released into systemic circulation. A menu command is displayed on display panel 20 for enabling the user to confirm that deflation of the cuff is intended. To continue with the initiated deflation, the user must intentionally confirm that deflation of the cuff is intended by means of a distinct and discrete manipulation of switch 22 by the user; in the preferred embodiment this distinct confirmation action requires the user to rotate switch 22 to select the confirmation menu command and then depress switch 22 within a 5 sec time period, at which confirmation the cuff is deflated. Alternatively if the user does not confirm the initiated deflation through a discrete manipulation and actuation of switch 22 within the 5 sec time period, then the initiated deflation is not carried out and the menu command for enabling the user to confirm that deflation was intended is removed from display panel 20.

If the user has made an automatic determination of recommended cuff pressure for cuff 4 and cuff 6 as described below, the safety interlock also operates as follows: if the user initiates deflation of cuff 4 or attempts to reduce the cuff 4 reference pressure to a level below the determined limb occlusion pressure for cuff 4 while the cuff 6 reference pressure or cuff 6 pressure is below the determined limb occlusion pressure for cuff 6 or attempts to deflate cuff 6 or reduce the cuff 6 reference pressure to a level below the determined limb occlusion pressure for cuff 6 while the cuff 4 reference pressure or cuff 4 pressure is below the determined limb occlusion pressure for cuff 4, a safety interlock signal is produced and a visual and audible warning is given via display panel 20 and speaker 68 to indicate to the user that the action the user has initiated may be unsafe, i.e. that the action would result in cuff 4 and cuff 6 being at a pressure which would allow blood flow at a time in a surgical procedure involving IVRA when liquid anesthetic agent contained in blood vessels distal to cuff 4 and cuff 6 may be released into systemic circulation. A menu command is displayed on display panel 20 for enabling the user to confirm that deflation of the cuff or cuff reference pressure adjustment is intended. To continue with the initiated deflation or cuff reference pressure adjustment, the user must intentionally confirm that deflation or adjustment of the cuff reference pressure to a level below limb occlusion pressure is intended by means of a distinct and discrete manipulation of switch 22 by the user; in the preferred embodiment this confirmation requires the user to rotate and then depress switch 22 within a 5 sec time period, at which confirmation deflation or the cuff reference pressure adjustment may proceed. Alternatively if the user does not confirm the initiated cuff deflation or cuff reference pressure adjustment through a discrete manipulation and actuation of switch 22 within the 5 sec time period, then the initiated deflation or adjustment is not carried out and the menu command for enabling the user to confirm that reduction of cuff pressure was intended is removed from display panel 20.

In this manner, the safety interlock mechanism for IVRA detects a potentially unsafe action initiated by the operator's selection of a command, produces a safety interlock signal and generates visual and audible indications to warn the operator of the potentially unsafe action which has been initiated, and prevents the initiated action from being implemented unless and until a distinct confirmation action is performed by the operator. Although the preferred embodiment of the safety interlock mechanism is described above, it will be appreciated by those normally skilled in the art that alternate mechanisms and embodiments may be employed. For example, an alternate embodiment of the safety interlock mechanism can be employed in any dual cuff tourniquet apparatus to detect any potentially unsafe attempt to deflate or reduce the pressure in one of the dual cuffs to a non-zero level, if the result of that attempt to depressurize or reduce the pressure in the cuff may be to allow the release of anesthetic agent past the cuff and into systemic circulation when the dual cuff tourniquet apparatus is used in conjunction with IVRA. Also, an alternate embodiment of the safety interlock mechanism may employ only an audible warning, or only a visual warning, or may generate no warning directly but may instead make the safety interlock signal available for integration with other monitoring and display systems in the operating room. Further, an alternate embodiment of the safety interlock apparatus may employ other means for enabling the user to confirm that a potentially unsafe reduction of cuff pressure is intended; for example, a separate confirmation switch may be provided for actuation by the user at any time after the detection of the potentially unsafe attempt, or confirmation may require that multiple actuations of the same switch be performed by the user within a specified time period, or confirmation may require that two switches be depressed simultaneously by the user.

To provide the user of instrument 2 with a detailed record of applied pressures and alarm conditions, event register 58 is provided. "Events" which are defined in the software of the preferred embodiment to be: (a) actions by the user to inflate a cuff, deflate a cuff, adjust the level of a cuff reference pressure signal, adjust the level of cuff inflation time limit signal, adjust the level of the operating mode signal or silence an audio alarm; (b) alarm events, resulting from microprocessor 28 generating an alarm signal as described above; and (c) events associated with determining a cuff pressure automatically as described below. Microprocessor 28 communicates with event register 58 to record events as they occur. Microprocessor 28 records an event by communicating to event register 58: the time of the event as read from real time clock 52; a value identifying which one of a specified set of events occurred as determined by microprocessor 28; and the values at the time of the event of the following parameters: operating mode signal, cuff 4 pressure signal; cuff 4 pressure reference signal; cuff 4 inflation time, cuff 4 inflation time limit; cuff 6 pressure signal; cuff 6 pressure reference signal; cuff 6 inflation time, cuff 6 inflation time limit; and recommended cuff pressure, when the event occurred. Entries are recorded in event register 58 by storing values in event register memory 60 and by printing these values for the user by means of event register printer 62. In operation, the user can erase from the event register 58 previously registered events and prepare event register 58 to retain new events.

The user, by means of selecting a menu command shown on display panel 20, can cause descriptions of the events recorded in event register memory 60 to be printed on event register printer 62. For each recorded event, microprocessor 28 causes to be printed the time of the event, a text message describing the event, and the parameters recorded at the time of the event.

In operation prior to the inflation of cuff 4 the user may instruct microprocessor 28 by using switch 22 to select the "RECOMMEND CUFF PRESSURE" command on menu 72, thus beginning the automatic determination of a recommended cuff pressure level for cuff 4. To determine a recommended cuff pressure microprocessor 28 first ensures that an adequate blood flow signal is being produced by sensor 10. Microprocessor 28 then sets to 50 mmHg the value of the cuff pressure reference signal for cuff 4 which causes the pressure in cuff 4 to increase to 50 mmHg. Next, microprocessor 28 measures and stores the level of the blood flow signal being produced by sensor 10. Microprocessor 28 then increases, in discrete steps of 10 mmHg or 5 mmHg as described below, the value of the cuff 4 pressure reference signal up from 50 mmHg. If the level of the current blood flow signal from sensor 10 is greater than or equal to 50 percent of the previously stored blood flow signal level, microprocessor 28 increases the cuff 4 pressure reference signal in steps of 10 mmHg. If the level of the current blood flow signal from sensor 10 is less than 50 percent of the previously stored blood flow signal, microprocessor 28 increases the cuff 4 pressure reference signal in steps of 5 mmHg. Microprocessor 28 continues to increase the pressure reference signal for cuff 4, and thereby the pressure in cuff 4, until the pressure reference signal for cuff 4 exceeds 300 mmHg or the level of the current blood flow signal from sensor is less than 3 percent of the previously stored blood flow signal level. If the cuff 4 reference level exceeds 300 mmHg the determination of a recommended cuff pressure is terminated and the user of instrument 2 informed by messages displayed on display panel 20 that the determination was unsuccessful. The level of the pressure signal from cuff 4 corresponding to the lowest level at which the level of the current blood flow signal from sensor 10 is less than 3 percent of the previously stored blood flow signal level is displayed as the Limb Occlusion Pressure and is used to calculate the Recommended Cuff Pressure, as follows. If the Limb Occlusion Pressure is less than or equal to 130 mmHg a safety margin of 40 mmHg is added to estimate the Recommended Cuff Pressure; if the Limb Occlusion Pressure is greater than 130 mmHg and no greater than 190 mmHg, a safety margin of 60 mmHg is added to estimate the Recommended Cuff Pressure; and if the Limb Occlusion Pressure is greater than 190 mmHg, a safety margin of 80 mmHg is added to estimate the Recommended Cuff Pressure. This Recommended Cuff Pressure level is displayed on display panel 20 and the cuff pressure reference signal is adjusted by microprocessor 28 to be equivalent to the level of the Recommended Cuff Pressure.

Additionally, prior to the inflation of cuff 6 when cuff 6 is used in addition to cuff 4 for either "IVRA Dual Bladder Cuff Mode" or "Dual Cuff Mode", the user may instruct microprocessor 28 by means of switch 22 to automatically determine the Recommended Cuff Pressure level for cuff 6. The process for determining the Recommended Cuff Pressure for cuff 6 is the same as that described above for cuff 4.

III. Software

FIGS. 4, 5, 6, 7, 8 and 9 are software flow charts depicting the sequence of operations which microprocessor 28 is programmed to carry out in the preferred embodiment of the invention. In order to simplify the discussion of the software, a detailed description of each software subroutine and of the control signals which the software produces to actuate the hardware described above is not provided. It will however be understood by those skilled in the art that, for example, in order to display characters and graphics on display panel 20, microprocessor 28 must generate appropriate signals and communicate them to display controller 64. Functions or steps carried out by the software are described below and related to the flow charts via parenthetical reference numerals in the text.

Software for the preferred embodiment was developed using the C programming language and compiled with C96 (Intel Corp. Santa Clara, Calif.).

Figure 4:
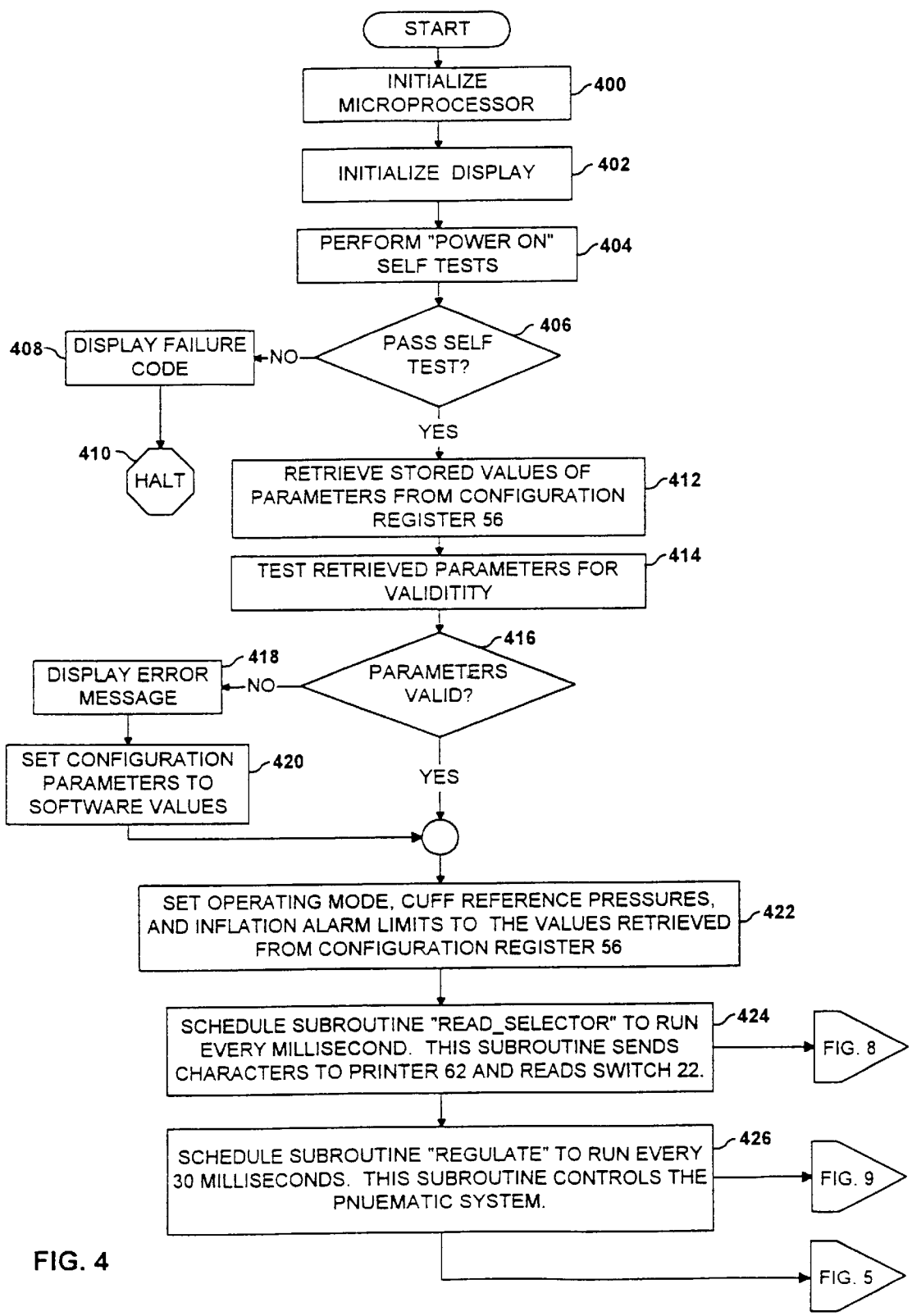
FIGS. 4, 5, 6, 7, 8 and 9 are software flow charts depicting the control software of the preferred embodiment.
Figure 5:
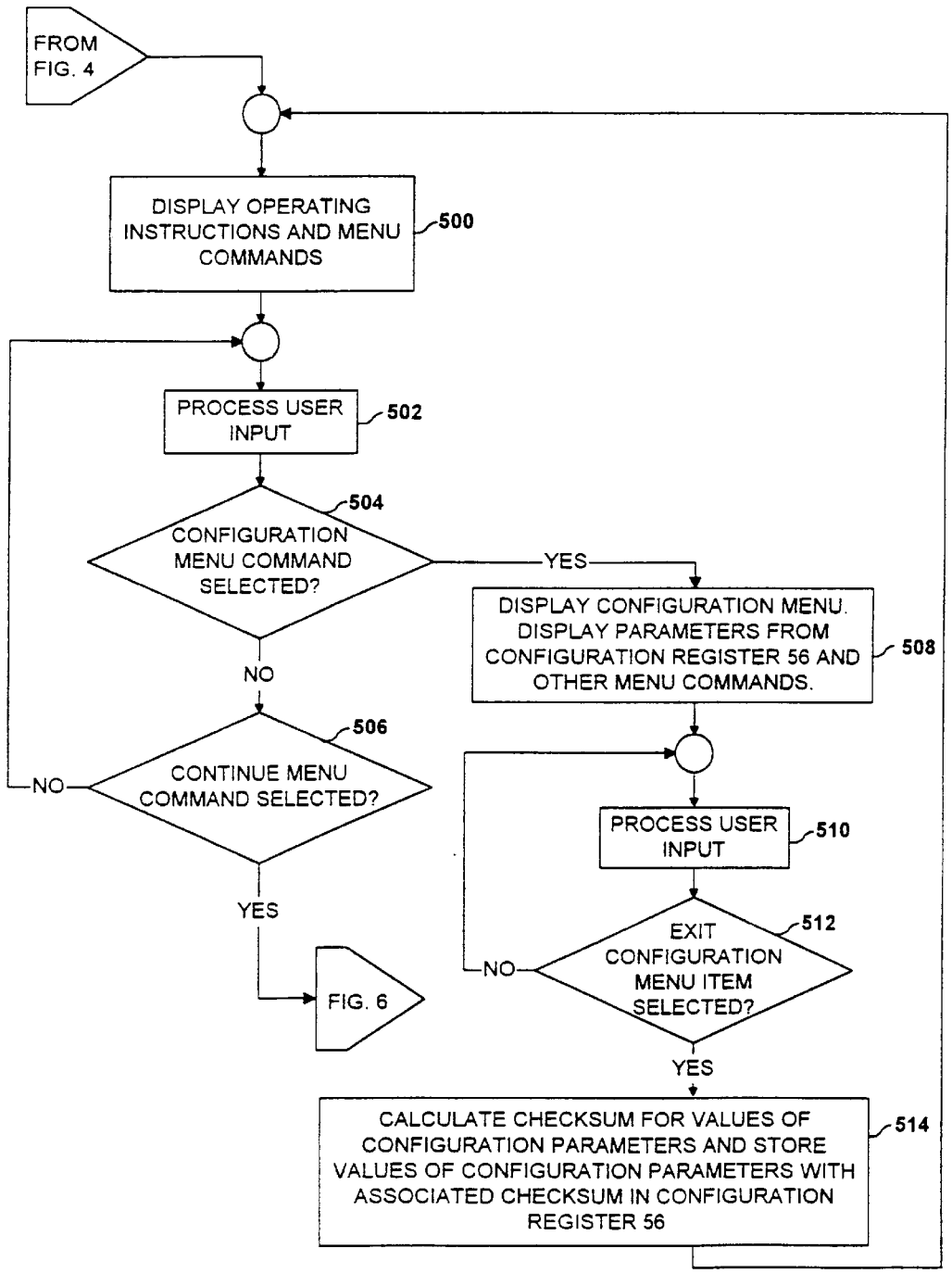
Figure 6:
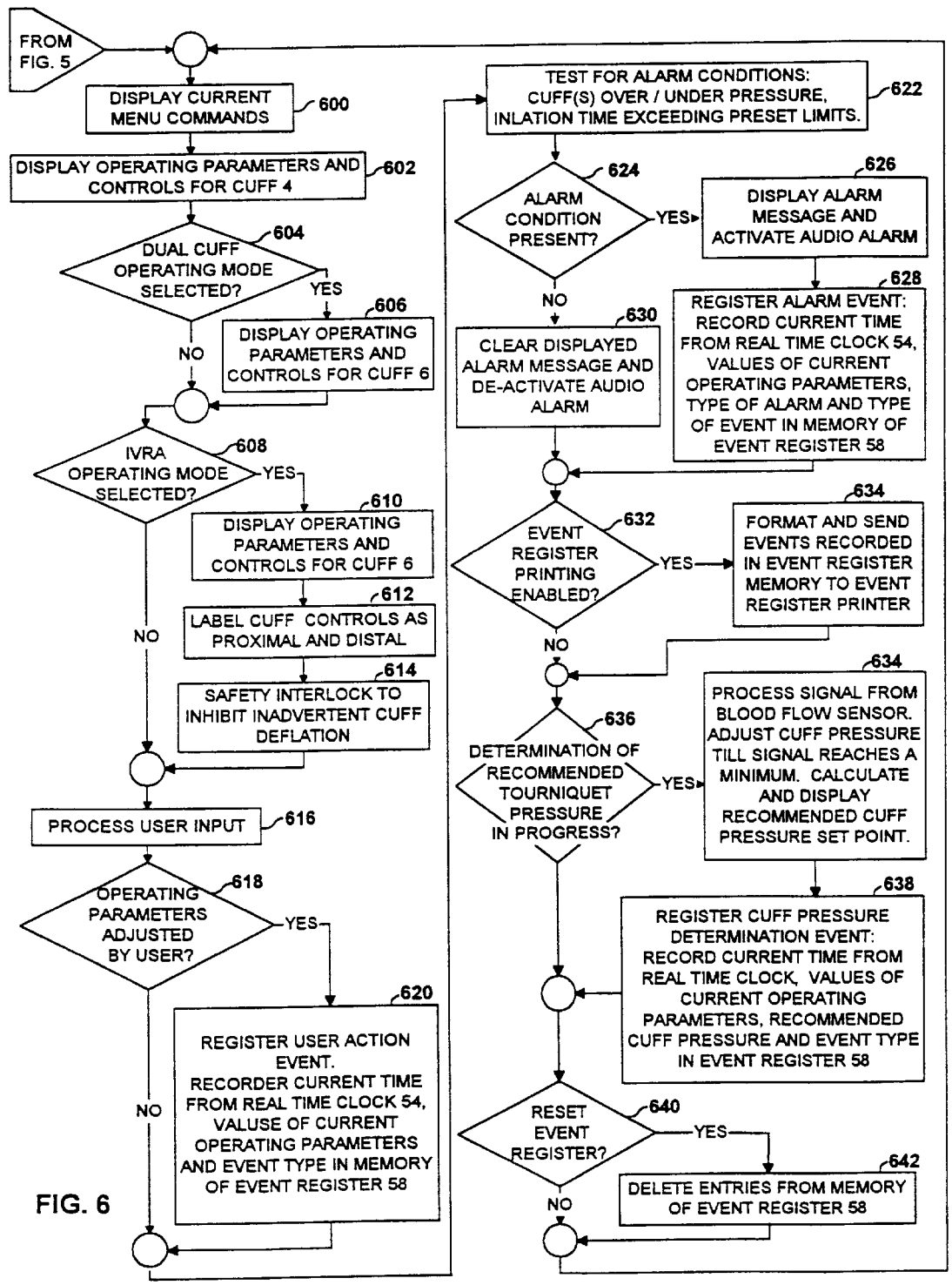
Figure 7:
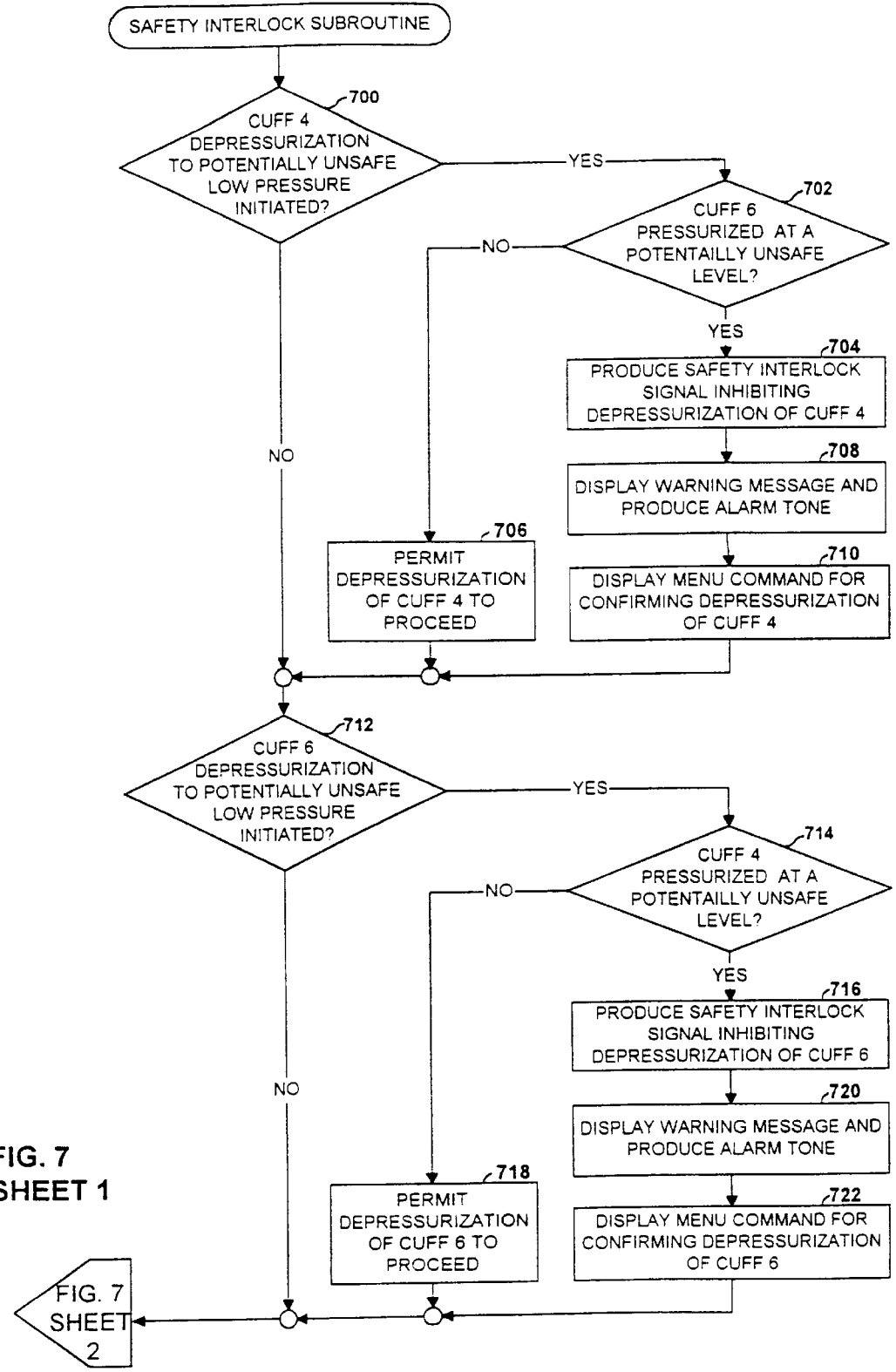
Figure 8:
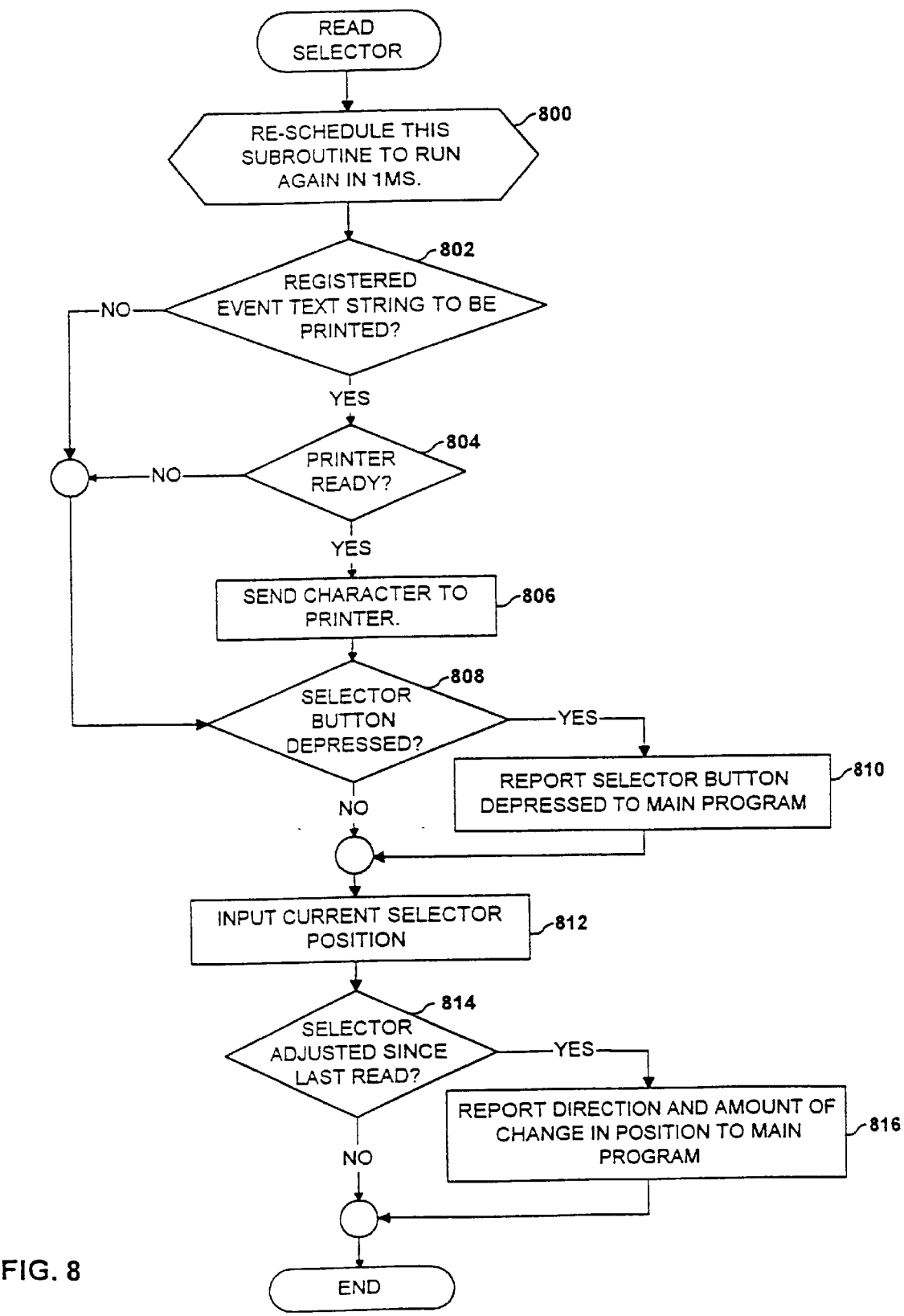
Figure 9:
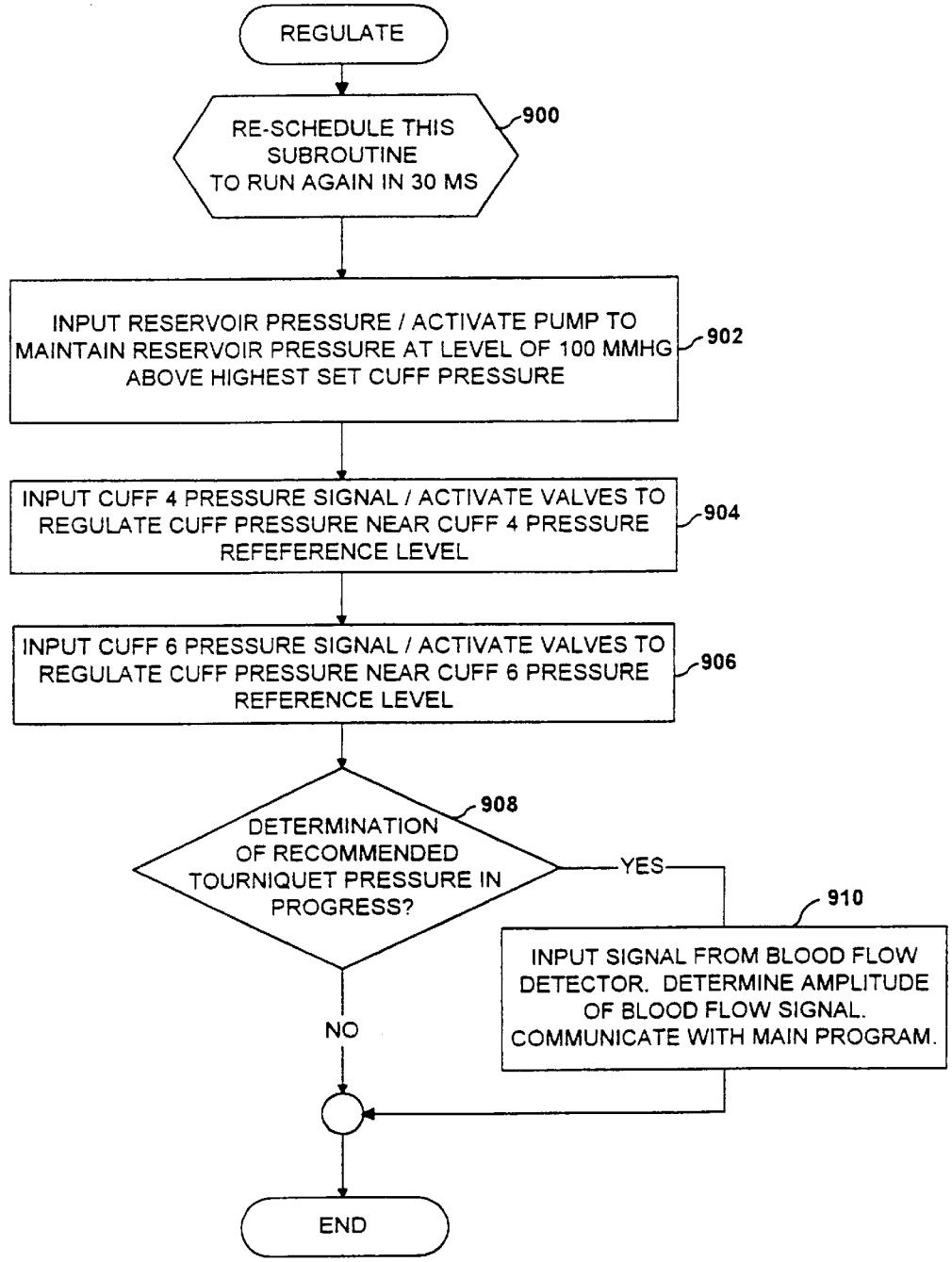

The main program software is depicted in FIGS. 4, 5, 6 and 7, and the utility software subroutines "read selector" and "regulate" are shown in FIGS. 8 and 9 respectively. FIG. 4 shows the initialization operations carried out by the main program. FIG. 5 shows the operations taken to adjust and record user configuration parameters. FIG. 6 shows the main program control loop entered at the completion of the initialization operations. FIG. 7 shows the operation of the safety interlock subroutine.

As shown in FIG. 4, the program commences (400) when power is supplied to microprocessor 28 by initializing microprocessor 28 for operation with the memory system and circuitry and hardware of the preferred embodiment. Display controller 64 is then initialized (402) with the parameters required for operation with display panel 20. Control is then passed to a self-test subroutine (404). The self-test subroutine displays a "SELF TEST IN PROGRESS" message on display panel 20 and performs a series of diagnostic tests to ensure proper operation of microprocessor 28 and its associated hardware. Should any diagnostic test fail (406), an error code is displayed on display panel 20 (408) and further operation of the system is halted (410); if no errors are detected, control is returned to the main program.

As can be seen in FIG. 4, after the "self-test" has been completed successfully, control is next passed to a subroutine (412) which retrieves from configuration register 56 the levels of previously recorded configuration parameters. The parameters are: a level for the operating mode signal and, for each of the three possible levels of the operating mode signal, a level for the cuff reference pressure and cuff inflation time alarm limit for each cuff. Upon completion, this subroutine returns control to the main program. Control is next passed to a subroutine (414) which tests the retrieved configuration parameters for validity by: (1) calculating a checksum for the retrieved levels of the parameters and comparing it to a checksum previously calculated and recorded in configuration register 56; (2) testing each retrieved parameter level to ensure it is within pre-defined allowable limits. If any of the retrieved parameters are found to be invalid (416) an error message is displayed on display panel 20 (418), and configuration parameters are set to default levels is defined in software (420). Control is then returned to the main program, where the operating mode signal, the levels for the cuff reference pressures, and the alarm limits are set to the values of the previously recorded configuration parameters (422).

As shown in FIG. 4, the software subroutine "read selector" which processes user input from switch 22 and sends characters to event register printer 62, is then scheduled to run every millisecond (424). This subroutine is initiated by the software timer interrupt system of microprocessor 28 and communicates with the main program by means of global variables. The flow chart for this subroutine is shown in detail in FIG. 8 and is discussed below. The software subroutine "regulate", for controlling the pneumatic system and inputting signals from photoplethysmographic blood flow sensor 10, is then scheduled to run every 30 milliseconds (426). This subroutine is initiated by the software timer interrupt system of microprocessor 28 and communicates with the main program by means of global variables. The flow chart for this subroutine is shown in detail in FIG. 9 and is discussed below. The flow chart for the main program is continued in FIG. 5.

Figure 3D:
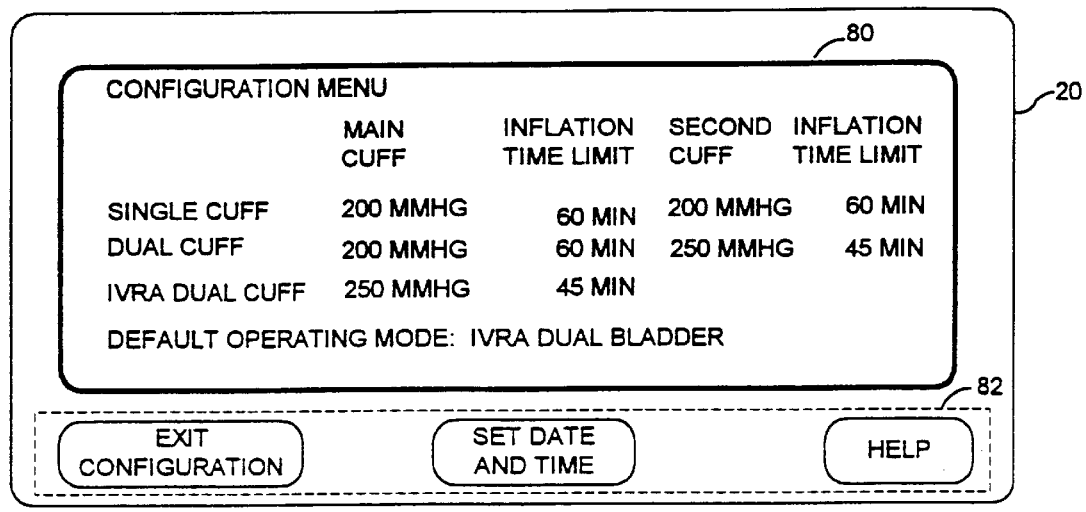

As shown in FIG. 5, the operation of the main program continues by passing control to a subroutine (500) which displays on display panel 20 basic operating instructions and menu commands which allow the user either to choose a menu command to "CONTINUE" with the operation of the preferred embodiment or to choose a menu command to "CONFIGURE" the preferred embodiment. Control is then passed to a "process user input" subroutine (502) for processing user input, as follows: the subroutine communicates with the subroutine "read selector" via global variables, updates displayed menu choices and values of parameters in response to the rotation and activation of switch 22; and passes control to other subroutines or parts of the main program based on menu commands selected by the user. The processing of user input by this subroutine continues until the user selects either the "CONFIGURE" (504) or "CONTINUE" (506) menu commands. If the user selects the "CONTINUE" menu command control returns to the main program and continues as detailed in FIG. 6. If the user chooses the "CONFIGURE" menu command, control is passed to a subroutine (508) which displays the levels of parameters retained in configuration register 56 and associated menu commands; these parameters and menu commands are depicted in display region 80 labeled CONFIGURATION MENU and menu 82 shown in FIG. 3d. Control is next passed to a subroutine (510) for processing user input similar to the subroutine described above; this subroutine updates the displayed parameters and menu commands to indicate adjustments made by the user. The processing of user input continues until a menu command for exiting the configuration menu is selected by the user (512), as shown in menu 82 in FIG. 3d. As can be seen in FIG. 5, control is then passed to a subroutine (514) which calculates a checksum for the levels of the configuration parameters and records the levels of the configuration parameters along with their associated checksum in configuration register 56. Control is then returned to the subroutine (500) for displaying basic operating instructions and "CONTINUE" and "CONFIGURE" menu commands, and operation continues as described above.

The flow chart depicted in FIG. 6 shows the main program control loop entered in response to the "CONTINUE" menu command being selected as described above. As shown in FIG. 6 the main program then enters a loop which continues until electrical power required for the operation of microprocessor 28 is interrupted.

As depicted in FIG. 6, control is first passed to a subroutine (600) which displays on display panel 20 menu commands for controlling the operation of the preferred embodiment. These menu commands are shown in FIG. 3a as menu 72, which enables choices to be made by the user for: temporarily silencing audio alarms; printing on event register printer 62 the events recorded in event register memory 60; initiating the determination of recommended cuff pressure; selecting an operating mode, or obtaining operating instructions. Control is then returned to the main program.

Control is next passed to a subroutine (602) which displays on display panel 20 operating parameters and controls referring only to cuff 4. The operating parameters include the current level of cuff pressure, cuff pressure reference level, inflation time and inflation time alarm limit. The menu commands for control of cuff 4 comprise: menu commands for cuff inflation and cuff deflation. These operating parameters and controls are depicted in display region 70 labeled MAIN CUFF shown in FIG. 3a. Upon completion of this subroutine control is returned to the main program.

If the operating mode signal described above is set to "Dual Cuff Mode" (604), control is passed to a subroutine (606) which displays on display panel 20 the operating parameters and menu commands for controlling cuff 6. The parameters and menu commands are identical to those described above for cuff 4. These operating parameters and controls are depicted in display region 74 labeled SECOND CUFF shown in FIG. 3a. Upon completion this subroutine returns control to the main program.

If the operating mode signal described above is set to "IVRA Dual Bladder Cuff Mode" (608) control is passed to a subroutine (610) which displays on display panel 20 the operating parameters and menu commands for controlling cuff 6. Control is then passed to a subroutine (612) which identifies the controls and parameters for cuff 4 as referring to the PROXIMAL CUFF and the controls and parameters for cuff 6 as referring to the DISTAL. This is depicted in FIG. 3c by display region 76 labeled PROXIMAL CUFF and display region 78 labeled DISTAL CUFF. As shown in FIG. 6, control is next passed to a "safety interlock" subroutine (614) to reduce the probability of unintended and inadvertent deflation of both cuff 4 and cuff 6 during a surgical procedure involving IVRA. The "safety interlock" subroutine functions as described below and depicted in FIG. 7.

The safety interlock subroutine shown in FIG. 7 commences by testing whether depressurization of cuff 4 to a potentially unsafe low pressure has been initiated by the user (700), either by selecting a menu command for the deflation of cuff 4 and activating switch 22, or by selecting the cuff 4 reference pressure and adjusting it to a pressure below a level representing the minimum pressure which will stop blood flow and the release of anesthetic agent past cuff 4; if so, the state of cuff 6 is then tested (702) and if cuff 6 is deflated or pressurized below a level representing the minimum pressure which will stop blood flow and the release of anesthetic agent past cuff 6, a safety interlock signal is generated (704) which prevents the initiated deflation of cuff 4 or initiated cuff 4 reference pressure adjustment from occurring in the absence of user confirmation; otherwise the safety interlock signal is not produced and cuff 4 deflation or reference pressure adjustment proceeds (706). In the preferred embodiment, a cuff is defined to be deflated if the cuff pressure is less than a level of 10 mmHg, and the level representing the minimum pressure which will stop blood flow and the release of anesthetic agent past a cuff is set to be the Limb Occlusion Pressure for that cuff determined automatically as described above. It will be appreciated by those normally skilled in the art that alternate mechanisms and embodiments may be employed for determining and setting the pressure levels used in testing the states of cuffs; for example, the levels may be preset to other pressures, or the preset levels may be adjustable by a user. After producing a safety interlock signal (704) control is passed to a subroutine (708) for displaying a warning message on display panel 20 and generating an audio alarm tone. Control is next passed to a subroutine (710) which displays a menu command for requiring the user to confirm that the deflation or depressurization of cuff 4 below the level is intended while cuff 6 is deflated or pressurized to the low level. The safety interlock subroutine continues by testing whether depressurization of cuff 6 to a potentially unsafe low pressure has been initiated by the user (712), either by selecting a menu command for the deflation of cuff 6 and activating switch 22, or by selecting the cuff 6 reference pressure and adjusting it to a pressure below a level representing the minimum pressure which will stop blood flow and the release of anesthetic agent past cuff 6; if so, the state of cuff 4 is then tested (714) and if cuff 4 is deflated or pressurized below a level representing the minimum pressure which will stop blood flow and the release of anesthetic agent past cuff 4, a safety interlock signal is generated (716) which prevents the initiated deflation of cuff 6 or initiated cuff 6 reference pressure adjustment from occurring in the absence of user confirmation; otherwise the safety interlock signal is not produced and cuff 6 deflation or reference pressure adjustment proceeds (718). After producing a safety interlock signal (716) control is passed to a subroutine (720) for displaying a warning message on display panel 20 and generating an audio alarm tone. Control is next passed to a subroutine (722) which displays a menu command for requiring the user to confirm that the deflation or depressurization of cuff 6 below the level is intended while cuff 4 is deflated or pressurized to the low level.

As shown in FIG. 7 the safety interlock subroutine continues by testing (724) whether a menu command for confirming the potentially unsafe deflation or depressurization of cuff 4 is currently displayed on display panel 20. If the menu command has been displayed for greater than 5 seconds (726), control is passed to a subroutine (728) for removing from display panel 20 and thereby making unavailable to the user the menu command for confirming the deflation or depressurization of cuff 4. If the menu command for confirming the deflation or depressurization of cuff 4 is displayed, and is selected by the user and switch 22 is activated (730), control is passed to a subroutine (732) for producing a confirmation signal which will permit the initiated deflation or depressurization of cuff 4 to proceed. The safety interlock subroutine continues by testing (734) whether a menu command for confirming the potentially unsafe deflation or depressurization of cuff 6 is currently displayed on display panel 20. If the menu command has been displayed for greater than 5 seconds (736), control is passed to a subroutine (738) for removing from display panel 20 and thereby making unavailable to the user the menu command for confirming the deflation or depressurization of cuff 6. If the menu command for confirming the deflation or depressurization of cuff 6 is displayed, and is selected by the user and switch 22 is activated (740), control is passed to a subroutine (742) for producing a confirmation signal which will permit the initiated deflation or depressurization of cuff 6 to proceed. Control is then returned to the main program depicted in FIG. 6.

Referring to the flowchart depicted in FIG. 6, it can be seen that if the operating mode signal is set to "Single Cuff Mode", only the controls and parameters referring to cuff 4 will be displayed and available to the user.

As can be seen in FIG. 6, after completion of specific operations related to the specific level of the operating mode signal, control then passes to a "process user input" subroutine (616) for processing user input, and this subroutine communicates with the subroutine "read selector" via global variables to update the currently displayed menu commands and parameters in response to the rotation and activation of switch 22. This subroutine may also pass control to other subroutines or parts of the main program based on menu commands selected by the user. Upon completion, this subroutine returns control to the main program.

As indicated in FIG. 6, if the user has initiated an event (618) by inflating a cuff, deflating a cuff, adjusting the level of a cuff reference pressure signal, adjusting the level of cuff inflation time limit signal, adjusting the level of the operating mode signal or silence an audio alarm; control is next passed to a subroutine (620) which records the event in event register 58. An event is recorded by communicating to event register 58: the time of the event as read from real time clock 52; a value identifying which one of a specified set of events occurred; and the values at the time of the event of the following parameters: operating mode signal, cuff 4 pressure signal; cuff 4 pressure reference signal; cuff 4 inflation time, cuff 4 inflation time limit; cuff 6 pressure signal; cuff 6 pressure reference signal; cuff 6 inflation time, cuff 6 inflation time limit; and recommended cuff pressure, when the event occurred. Control is then returned to the main program.

As shown in FIG. 6, control in the main program loop is next passed to subroutine (622) which tests for alarm conditions. If an alarm condition is present (624), such as cuff over-pressurization, cuff under-pressurization, or exceeding an inflation time limit, control is passed to a subroutine (626) which initiates the generation of an alarm tone and displays on display panel 20 pre-assigned text messages indicating the cuff to which the alarm refers and the actual alarm condition present. Control is next passed to a subroutine (628) which records the alarm event in event register 58. An alarm event is recorded by communicating to event register 58: the time of the event as read from real time clock 52; a value identifying which one of a specified set of alarm events occurred; and the values at the time of the event of the following parameters: operating mode signal, cuff 4 pressure signal; cuff 4 pressure reference signal; cuff 4 inflation time, cuff 4 inflation time limit; cuff 6 pressure signal; cuff 6 pressure reference signal; cuff 6 inflation time, cuff 6 inflation time limit; and recommended cuff pressure, when the event occurred. Control is then returned to the main program. If alarms conditions are not present at the completion of the test for alarm conditions, control is passed to a subroutine (630) for clearing any previously displayed alarm messages and deactivating, if active, the audio alarm. Control is then returned to the main program.

If the user has, by means of selecting the appropriate menu command, enabled the printing of events (632), then control is next transferred to a subroutine (634) to format and send registered events to the printer. This subroutine retrieves events from the event register 58, formats the retained event information as an ASCII text string suitable for printing on event register printer 62 and signals the subroutine "read selector" which sends characters to the printer that a string is available be printed. Control is then returned to the main program.

Also as indicated in FIG. 6, if the user has initiated a determination of recommended cuff pressure for cuff 4 or cuff 6 if alternatively selected by the user (634), control is passed to a subroutine for doing so. This subroutine (636) controls the sequencing of cuff inflation and deflation and performs the activities related to determining a recommended a cuff pressure as follows. If the user has selected a determination for cuff 4, the blood flow signal from sensor 10 is first analyzed and shown on display panel 20. The value of the cuff pressure reference signal for cuff 4 is then set to 50 mmHg which causes the pressure in cuff 4 to increase to 50 mmHg. Next, the level of the blood flow signal being produced by sensor 10 is stored. The cuff 4 pressure reference signal is then increased up from 50 mmHg in discrete steps of 10 mmHg or 5 mmHg as follows. If the level of the current blood flow signal from sensor 10 is greater than or equal to 50 percent of the previously stored blood flow signal level, the cuff 4 pressure reference signal is increased in steps of 10 mmHg. If the level of the current blood flow signal from sensor 10 is less than 50 percent of the previously stored blood flow signal, the cuff 4 pressure reference signal is increased in steps of 5 mmHg. The pressure reference signal for cuff 4, and thereby the pressure in cuff 4 continue to be increased until the pressure reference signal for cuff 4 exceeds 300 mmHg or the level of the current blood flow signal from sensor 10 is less than 3 percent of the previously stored blood flow signal level. If the cuff 4 reference level exceeds 300 mmHg the determination of a recommended cuff pressure is terminated and the user of instrument 2 informed by messages displayed on display panel 20 that the determination was unsuccessful. The level of the pressure signal from cuff 4 corresponding to the lowest level at which the level of the current blood flow signal from sensor 10 is less than 3 percent of the previously stored blood flow signal level is considered to represent the "Limb Occlusion Pressure" and is used to calculate the Recommended Cuff Pressure, as follows. If the Limb Occlusion Pressure is less than or equal to 130 mmHg a safety margin of 40 mmHg is added to estimate the Recommended Cuff Pressure; if the Limb Occlusion Pressure is greater than 130 mmHg and no greater than 190 mmHg, a safety margin of 60 mmHg is added to estimate the Recommended Cuff Pressure; and if the Limb Occlusion Pressure is greater than 190 mmHg, a safety margin of 80 mmHg is added to estimate the Recommended Cuff Pressure. This Recommended Cuff Pressure level is displayed on display panel 20 and the cuff pressure reference signal is adjusted by microprocessor 28 to be equivalent to the level of the Recommended Cuff Pressure. Alternatively, if the user has initiated a determination of Recommended Cuff Pressure for cuff 6, the subroutine performs the same steps as described above for cuff 4 except the cuff 6 pressure reference and cuff 6 pressure signals are used.

Control is next passed to a subroutine (638) which records in event register 58 the results of the determination. A recommend cuff pressure event is recorded by communicating to event register 58: the time of the event as read from real time clock 52; a value identifying which one of a specified set of events occurred; and the values at the time of the event of the following parameters: operating mode signal, cuff 4 pressure signal; cuff 4 pressure reference signal; cuff 4 inflation time, cuff 4 inflation time limit; cuff 6 pressure signal; cuff 6 pressure reference signal; cuff 6 inflation time, cuff 6 inflation time limit; and recommended cuff pressure, when the event occurred. Control is then returned to the main program.

As depicted in FIG. 6, the software includes provision for the user to delete all entries from event register 58. This might be desired by the user, for example, at the completion a surgical procedure. If the user has selected the appropriate menu command (640), control is passed to a subroutine (642) which deletes all entries in the event register. Control is then returned to the main program.

The main program shown in FIG. 6 continues by looping through the steps described above until such time as electrical power required for the operation of the preferred embodiment is removed or an error in program execution is detected and the program is halted by microprocessor 28.

The flow chart depicted in FIG. 8 refers to the subroutine "read selector". This subroutine is initiated by the software timer interrupt system of microprocessor 28 and runs asynchronously with the main program. The subroutine communicates with the main program through global variables. Upon entry, the subroutine schedules itself to run again in one millisecond (800). If an ASCII text string describing a registered event is to be printed (802), the status of event register printer 62 is polled and, if event register printer 62 is ready (804), a character is sent to event register printer 62 (806).

As next shown in FIG. 8, the status of the pushbutton of switch 22 is then polled to see if it is depressed (808): if it is, this is communicated to the main program (810). The current position of the selector portion of switch 22 is then polled (812) and, if the position of the selector has changed since the last time it was polled by this routine (814), the direction (clockwise or counter clockwise rotation) and amount of change in position is communicated to the main program (816). The subroutine then terminates, and restarts again one milliseconds after its last initiation.

The flow chart depicted in FIG. 9 refers to the subroutine "regulate". This subroutine controls the pneumatic system (pump 40, valve assemblies 26 and 38) and pre-processes input from sensor 10. This subroutine is also initiated by the software timer interrupt system of microprocessor 28 and runs asynchronously with the main program. The subroutine communicates with the main program through global variables.

As shown in detail in FIG. 9, upon entry, subroutine "regulate" schedules itself to run again in 30 ms (900). Next (902), the level of the pressure signal from pressure transducer 46 is read to indicate the pressure in reservoir 34 and compared to a reservoir reference pressure level which is set at 100 mmHg above the greater of the cuff 4 and cuff 6 reference pressure levels; if the pressure in the reservoir remains under the reference level by more than 20 mmHg for 300 ms, pump 40 is activated. If the pressure in the reservoir remains above the reference level by 20 mmHg for 300 ms, pump 40 is deactivated.

Also in subroutine "regulate" shown in FIG. 9, (904) the level of the pressure signal from pressure transducer 24 is read to indicate the pressure in cuff 4. This pressure is subtracted from the reference pressure for cuff 4, and the magnitude and polarity of the resulting difference signal is used to control the selection and opening times of valves within valve assembly 26, thereby regulating the pressure in cuff 4 at the reference level within +/−1 mmHg. For example, if the pressure in cuff 4 is lower than the reference pressure for cuff 4, microprocessor 28 opens low flow valve 1002 to introduce a controlled flow of gas into cuff 4 until the pressure in cuff 4 is within +/−1 mm Hg of the reference pressure. Microprocessor 28 then closes valve 1002. Similarly, excess pressure in cuff 4 would be exhausted until the pressure in cuff 4 is within the desired pressure range by opening low flow valve 1006 until a pressure signal from pressure transducer 24 is within a desired pressure range. The low flow valves 1002, 1006 permit more precise and controlled alteration of the pressure in cuff 4 than is permitted by higher flow valve 1004, 1010.

Also (906), the level of the pressure signal from pressure transducer 36 is read to indicate the pressure in cuff 6, if pressurized. This pressure is subtracted from the reference pressure for cuff 6, and the magnitude and polarity of the resulting difference signal is used to control the selection and opening times of valves within valve assembly 38, thereby regulating the pressure in cuff 6 at the reference level within +/−1 mmHg. Finally in subroutine "regulate", if a determination of recommended cuff pressure is in progress (908), the level of the blood flow signal from sensor 10 is read and processed (910). The amplitude of this blood flow signal is determined and communicated to the main program.

It is to be understood that the invention is not to be limited to the details herein given but may be modified within the scope of the appended claims.

We claim:

1. Safety apparatus for dual cuff tourniquet system, comprising:
   an inflatable and deflatable first cuff;
   an inflatable and deflatable second cuff;
   monitoring means for monitoring pressure in the first and second cuffs;
   control means for permitting an operator to initiate inflation of the first and second cuffs above a minimum pressure level, and for permitting an operator to initiate deflation of the first and second cuffs; and
   safety means connected to the monitoring means and to the control means for detecting the operator's attempt to initiate deflation of the second cuff while the pressure level in the first cuff is beneath the minimum pressure level.

2. The apparatus of claim 1 wherein the safety means includes interlock means for preventing deflation of the second cuff in the absence of the operator's manipulation of the apparatus to confirm the attempt to initiate deflation of the second cuff.

3. The apparatus of claim 2 wherein the safety means includes confirmation means for generating a confirmation signal in response to the operator's manipulation of the apparatus to confirm the attempt to initiate deflation of the second cuff, to which confirmation signal the control means responds for deflating the second cuff.

4. The apparatus of claim 3 wherein the safety means establishes a time period following the generation of the interlock signal during which period the operator's manipulation of the apparatus to confirm the attempt to initiate deflation of the second cuff will cause generation of the confirmation signal and after which period the operator's manipulation of the apparatus to confirm the attempt to initiate deflation of the second cuff will not cause generation of the confirmation signal.

5. The apparatus of claim 2 including alert means for providing a signal to the operator of the need for the operator's manipulation of the apparatus to confirm the attempt to initiate deflation of the second cuff.

6. The apparatus of claim 2 wherein the control means includes recommended pressure means for automatic determination of the minimum pressure level.

7. The apparatus of claim 2 wherein the control means includes reference pressure setting means for permitting the operator to establish the minimum pressure level at any pressure level within a range of pressure levels.

8. The apparatus of claim 2 wherein the minimum pressure level is less than about 10 mmHg.

9. The apparatus of claim 2 further comprising pressure regulating means for maintaining the pressure in the first and second cuffs at associated first and second predetermined levels.

10. The apparatus of claim 9 wherein the control means includes recommended pressure means for automatic determination of the minimum pressure level.

11. The apparatus of claim 9 wherein the control means includes reference pressure setting means for permitting the operator to establish the minimum pressure level at any pressure level within a range of pressure levels.

12. The apparatus of claim 9 further comprising:
   microprocessor means responsive to the control means and the safety means for producing a cuff mode signal and for setting the level of the cuff mode signal at either a first or second predefined level to indicate inflation or deflation of the cuff respectively, and further responsive to the pressure regulating means for setting the cuff mode signal at a third predefined level when the pressure in the cuff is to be maintained; and
   safety circuit means operable independently of the microprocessor means and responsive to the cuff mode signal and having a plurality of stored levels for the cuff mode signal, wherein the safety circuit means operates by comparing the level of the cuff mode signal to the plurality of stored levels for the cuff mode signal and producing a microprocessor fault signal when the cuff mode signal level does not correspond to one of the stored levels.

13. The apparatus of claim 9 wherein the pressure regulating means further comprises:
   at least one pressure source selectively pneumatically connected to the first and second cuffs; and
   at least one exhaust line selectively connected the first and second cuffs;
   wherein the control means senses preset undesired combinations of connection of each cuff to the pressure source and exhaust line and produces a fault signal in response to detection of any of the undesired combinations.

14. The apparatus of claim 13 wherein the fault signal stops the pressure regulating means from changing the pressure in the first and second cuffs.

15. The apparatus of claim 13 wherein the control means senses whether the safety apparatus is in a cuff deflating mode or cuff inflating mode, and produces the fault signal:

when at least one of the cuffs is in a cuff inflating mode and is connected to the exhaust line or disconnected from the pressure source; or when at least one of the cuffs is in a cuff regulating mode and is simultaneously connected to both the pressure source and exhaust line.

16. The apparatus of claim 15 wherein the pressure source is selectively pneumatically connected to one of the cuffs through separate first and second inlet valves that are actuated to connect the cuff to the pressure source, and the second inlet valve permits gas flow at a greater rate than the first inlet valve, and the exhaust line is selectively pneumatically connected to one of the cuffs through separate first and second exhaust valves which are actuated to connect the cuff to the exhaust line, wherein the second exhaust valve permits gas flow at a greater rate than the first exhaust valve, and wherein the control means produces the fault signal when:

the cuff is in a cuff deflating mode and either the first or second inlet valves is actuated, or both of the first and second exhaust valves are not actuated; and the cuff is in a cuff inflating mode and both of the first and second inlet valves are not actuated, or either of the first and second exhaust valves are actuated.

17. The apparatus of claim 16 wherein the control means produces the fault signal when the cuff is in a cuff regulating mode, and both the first inlet valve and first outlet valve are simultaneously actuated, or either of the second inlet valve or second outlet valve are actuated.

18. The apparatus of claim 9 further comprising:

a cuff mode signal from the pressure regulating means to indicate a mode in which the cuff is operating;

a first valve responsive to a first valve actuation signal and a first valve deactuation signal from the pressure regulating means, wherein the first valve is opened by the first valve actuation signal to pneumatically connect the pressure source to the cuff, or deactuated by the first valve deactuation signal to close the pneumatic connection between the cuff and pressure source;

a first valve status output signal from the first valve to indicate whether the first valve is open or closed;

a second valve responsive to a second valve actuation signal and second valve deactuation signal from the pressure regulating means, wherein the second valve is opened by the second valve actuation signal to pneumatically connect the pressure source to the cuff, or deactuated by the second valve deactuation signal to close the pneumatic connection between the cuff and pressure source;

a second valve status output signal from the second valve to indicate whether the second valve is open or closed; and a safety circuit that monitors the cuff mode signal and the first and second valve output signals for undesired combinations of cuff mode signal and first and second valve output signals, and produces a fault signal if an undesired combination is detected.

19. The apparatus of claim 18 further comprising:

a third valve responsive to a third valve actuation signal and third valve deactuation signal from the pressure regulating means, wherein the third valve is opened by the third valve actuation signal to pneumatically connect an exhaust line to the cuff, or deactuated by the third valve deactuation signal to close the pneumatic connection between the cuff and exhaust line;

a third valve status output signal from the third valve to indicate whether the third valve is open or closed;

a fourth valve responsive to a fourth valve actuation signal and a fourth valve deactuation signal from the pressure regulating means, wherein the fourth valve is opened by the fourth valve actuation signal to pneumatically connect the exhaust line to the cuff, or deactuated by the fourth valve deactuation signal to close the pneumatic connection between the cuff and exhaust line;

a fourth valve status output signal from the fourth valve to indicate whether the fourth valve is open or closed; and wherein the safety circuit monitors the cuff mode signal and the third and fourth valve output signals for undesired combinations of cuff mode signal and third and fourth valve output signals, and produces a fault signal if an undesired combination is detected.

20. The apparatus of claim 19 wherein production of the fault signal prevents actuation or deactuation of any of the first, second, third or fourth valves.

21. The apparatus of claim 1 wherein the minimum pressure level is that suitable for preventing blood flow past the first cuff within a limb to which the first and second cuffs are applied.

22. The apparatus of claim 21 wherein the safety means includes interlock means for generating an interlock signal to which the control means responds for preventing deflation of the second cuff in the absence of the operator's manipulation of the apparatus to confirm the attempt to initiate deflation of the second cuff.

23. A method for safely deflating cuffs in a dual cuff tourniquet apparatus that can be manipulated by an operator to separately initiate inflation and deflation of both of the cuffs, comprising the step of:

monitoring pressure levels in the first and second cuffs;

detecting the operator's attempt to initiate deflation of the second cuff while the pressure level in the first cuff is beneath a minimum pressure level; and preventing deflation of the second cuff in the absence of the operator's manipulation of the apparatus to confirm the detected attempt to initiate deflation of the second cuff while the pressure level in the first cuff is beneath the minimum pressure level.

24. Amended The method of claim 23 including the step of establishing as the minimum pressure level a pressure level that is suitable for preventing blood flow past the first cuff within a limb to which the tourniquet apparatus is applied.

* * * * *